(12) United States Patent
Crawley

(10) Patent No.: US 6,630,489 B1
(45) Date of Patent: Oct. 7, 2003

(54) QUINOLINE DERIVATIVES AS TYROSINE KINASE INHIBITORS

(75) Inventor: Graham Charles Crawley, Macclesfield (GB)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 09/913,864

(22) PCT Filed: Feb. 18, 2000

(86) PCT No.: PCT/GB00/00579

§ 371 (c)(1),
(2), (4) Date: Aug. 20, 2001

(87) PCT Pub. No.: WO00/50405

PCT Pub. Date: Aug. 31, 2000

(30) Foreign Application Priority Data

Feb. 24, 1999 (GB) .............................. 9904103

(51) Int. Cl.⁷ .................. A61K 31/47; A61K 31/415; C07D 213/00; C07D 215/00; C07D 207/00
(52) U.S. Cl. ................. 514/311; 514/314; 514/397; 514/398; 514/320; 544/106; 544/111; 544/363; 546/152; 546/153; 548/146; 548/300
(58) Field of Search .............. 514/231.5, 235.5, 514/252.13, 311, 314, 320, 365, 397, 398, 425; 544/106, 111, 358, 363, 402; 546/1, 26, 152, 153, 178, 183, 188, 216, 201, 229, 236, 242; 548/146, 183, 193, 400, 543, 556

(56) References Cited

FOREIGN PATENT DOCUMENTS

| WO | WO 98/52944 | 11/1993 |
|----|-------------|---------|
| WO | WO 96/09294 | 3/1996 |
| WO | WO 97/03069 | 1/1997 |
| WO | WO 98/02434 | 1/1998 |
| WO | WO 98/13350 | 4/1998 |
| WO | WO 98/43960 | 10/1998 |
| WO | WO 98/54156 | 12/1998 |
| WO | 9900372 | * 1/1999 |

* cited by examiner

Primary Examiner—Richard L. Raymond
Assistant Examiner—Sudhaker B. Patel
(74) Attorney, Agent, or Firm—Morgan, Lewis & Bockius LLP

(57) ABSTRACT

The invention concerns quinoline derivatives of formula (I) wherein n is 0–3 and each $R^4$, which may be the same or different, is a substituent such as halogeno, hydroxy, amino, nitro, trifluoromethyl, trifluoromethoxy, cyano or (1–6C) alkyl, or optionally substituted phenyl, phenoxy, anilino, N-(1–6C)alkylanilino, benzoyl or pyridyloxy; $R^1$ and $R^2$ is hydrogen or optionally substituted (1–6C)alkyl, (2–6C) alkenyl or (2–6C)alkynyl; or pharmaceutically-acceptable salts thereof; processes for their preparation, pharmaceutical compositions containing them and their use in the prevention or treatment of T cell mediated diseases or medical conditions

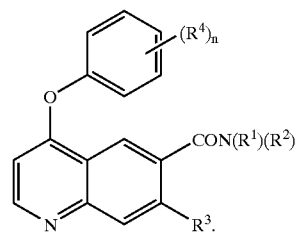

15 Claims, No Drawings

QUINOLINE DERIVATIVES AS TYROSINE KINASE INHIBITORS

This application is the National Phase of International Application PCT/GB00/00579 filed Feb. 18, 2000 which designated the U.S. and that International Application was published under PCT Article 21(2) in English.

This invention concerns certain novel quinoline derivatives which possess pharmacological properties of use in the treatment of autoimmune diseases or medical conditions, for example T cell mediated disease such as transplant rejection or rheumatoid arthritis. The invention also concerns processes for the manufacture of the quinoline derivatives of the invention, pharmaceutical compositions containing them and their use in therapeutic methods, for example by virtue of inhibition of T cell mediated disease.

A critical requirement of the immune system is the ability to differentiate between "self" and "non-self" (i.e. foreign) antigens. This discrimination is required to enable the immune system to mount a response to foreign proteins such as those on the surface of pathogens whilst maintaining tolerance to endogenous proteins and thereby preventing damage to normal tissues. An autoimmune disease results when self-tolerance breaks down and the immune system reacts against tissues such as the joints in rheumatoid arthritis or nerve fibres in multiple sclerosis. Stimulation of the human immune response is dependent on the recognition of protein antigens by T cells. However T cells do not become activated by and respond to antigen alone but are only triggered into action when the antigen is complexed with major histocompatibility complex (MHC) molecules on the surface of an antigen presenting cell such as a B cell, macrophage or dendritic cell.

Thus T cell activation requires the docking into the T cell receptor of the peptide/MHC complex expressed on an antigen presenting cell. This interaction, which confers the antigen specificity to the T cell response, is essential for full activation of T lymphocytes. Subsequent to this docking, some of the earliest signal transduction events leading to full T cell activation are mediated through the action of multiple tyrosine-specific protein kinases (E. Hsi et al., *J. Biol. Chem.*, 1989, 264, 10836) including $p56^{lck}$ and ZAP-70. The tyrosine kinase $p56^{lck}$ is a lymphocyte specific member of the src family of non-receptor protein tyrosine kinases (J. D. Marth et al., *Cell*, 1985, 43, 393). The enzyme is associated with the inner surface of the plasma membrane where it binds to the T cell receptor associated glycoproteins CD4 (in helper T cells) and CD8 (in cytotoxic or killer T cells) (C. E. Rudd et al., *Proc. Natl. Acad. Sci. USA*, 1988, 85, 5190 and M. A. Campbell et al, *EMBO J*, 1990, 9, 2125).

It is believed that $p56^{lck}$ tyrosine kinase plays an essential role in T cell activation as, for example, the loss of $p56^{lck}$ expression in a human Jurkat T cell line prevents the normal T cell response to stimulation of the T cell receptor (D. B. Straus et al., *Cell*, 1992, 70, 585) and a deficiency in $p56^{lck}$ expression causes severe immune deficiency in humans (F. D. Goldman et al., *J. Clin. Invest.*, 1998, 102, 421).

Certain autoimmune conditions or diseases such as inflammatory diseases (for example rheumatoid arthritis, inflammatory bowel disease, glomerulonephritis and lung fibrosis), multiple sclerosis, psoriasis, hypersensitivity reactions of the skin, atherosclerosis, restenosis, allergic asthma and insulin-dependent diabetes are believed to be associated with inappropriate T cell activation (see, for example, J. H. Hanke et al, *Inflamm. Res.*, 1995, 44, 357). In addition the acute rejection of transplanted organs can also be interpreted as a consequence of inappropriate T cell activation. Therefore, compounds which modulate T cell activation by way of inhibition of one or more of the multiple tyrosine-specific protein kinases which are involved in the early signal transduction steps which lead to full T cell activation, for example by way of inhibition of $p56^{lck}$ tyrosine kinase, are expected to provide therapeutic agents for such pathological conditions.

Without wishing to imply that the compounds disclosed in the present invention possess pharmacological activity only by virtue of an effect on a single biological process, it is believed that the compounds modulate T cell activation by way of inhibition of one or more of the multiple tyrosine-specific protein kinases which are involved in the early signal transduction steps which lead to full T cell activation, for example by way of inhibition of $p56^{lck}$ tyrosine kinase.

In particular, the quinoline derivatives of the invention are expected to be useful as immunoregulation or immunosuppressive agents for the prevention or treatment of organ rejection following transplant surgery.

Agents of this kind would offer therapy for transplant rejection and autoimmune diseases whilst avoiding toxicities associated with the commonly used, less selective immunosuppressants. The leading agent for the prevention or treatment of transplant rejection is cyclosporin A which, although effective, is often associated with side-effects such as renal damage and hypertension which results in kidney failure in a substantial number of patients. It is contemporary practice to treat rheumatoid arthritis initially with symptom relief agents such as NSAIDs, which do not have any beneficial effect on disease progression and are often associated with unwanted side-effects. A rationally based, disease modifying agent, without such deleterious side-effects, would therefore offer significant benefits in the prevention or treatment of transplant rejection or autoimmune conditions such as rheumatoid arthritis.

The present invention is based, in particular, on the discovery that the quinoline derivatives of the invention modulate T cell activation by way of inhibition of one or more of the multiple tyrosine-specific protein kinases which are involved in the early signal transduction steps which lead to full T cell activation. Accordingly compounds of the present invention possess higher inhibitory potency against particular non-receptor tyrosine kinases such as $p56^{lck}$ tyrosine kinase than against other non-receptor tyrosine kinases or against receptor tyrosine kinases (RTKs) such as epidermal growth factor (EGF) RTK or vascular endothelial growth factor (VEGF) RTK. Nevertheless, whilst the quinoline derivatives of the present invention are generally potent inhibitors of $p56^{lck}$ tyrosine kinase, they do also, in general, possess weaker activity against certain other tyrosine kinase enzymes. In particular, the quinoline derivatives of the present invention, in general, possess some inhibitory activity against EGF RTK and, in general, they may possess some weaker activity against VEGF RTK.

In general, the quinoline derivatives of the invention possess sufficient potency in inhibiting non-receptor tyrosine kinases such as $p56^{lck}$ tyrosine kinase that they may be used in an amount sufficient to inhibit, for example, $p56^{lck}$ tyrosine kinase whilst demonstrating reduced potency, preferably whilst demonstrating no significant activity, against RTKs such as EGF RTK or VEGF RTK. Thus the quinoline derivatives of the invention can be used in the clinical management of those particular diseases which are sensitive to inhibition of such non-receptor tyrosine kinases, for example autoimmune diseases or medical conditions, for example T cell mediated disease such as transplant rejection or rheumatoid arthritis.

Nevertheless, at appropriate higher doses, the quinoline derivatives of the present invention demonstrate pharmacologically useful inhibition of other tyrosine kinase enzymes, for example of RTKs such as EGF RTK and/or VEGF RTK. In that event, the quinoline derivatives of the invention are also useful in the treatment of further tyrosine kinase dependent diseases or conditions such as EGF-sensitive cancers and VEGF-sensitive angiogenesis.

It is disclosed in International Patent Application WO 96/09294 that certain quinoline and quinazoline derivatives may be useful as protein tyrosine kinase inhibitors. Whilst a few 4-benzyloxy- and 4-phenoxy-quinazoline derivatives were disclosed, there was no disclosure of any examples of 4-benzyloxy- or 4-phenoxy-quinoline derivatives.

It is disclosed in International Patent Application WO 97/03069 that certain quinoline and quinazoline derivatives may be useful as protein tyrosine kinase inhibitors. All of the disclosed examples were 4-heteroarylaminoquinazoline derivatives and none of them were 4-heteroarylmethoxy- or 4-heteroaryloxy-quinazoline derivatives.

It is disclosed in International Patent Application WO 98/13350 that certain quinoline derivatives may be useful in the production of an antiangiogenic and/or vascular permeability reducing effect. Whilst certain 4-phenoxyquinoline derivatives are disclosed, there is no disclosure of any such compounds which possess a carboxy, alkoxycarbonyl, carbamoyl or N-alkylcarbamoyl substituent on the quinoline ring.

It is disclosed in International Patent Application WO 98/43960 that certain 3-cyanoquinoline derivatives may be useful as protein tyrosine kinase inhibitors. Almost all of the 398 disclosed examples were 3-cyano-4-anilinoquinoline or 3-cyano-4-benzylaminoquinoline derivatives. There was the disclosure of a single 3-cyano-4-phenoxyquinoline derivative but there was no disclosure of any such compounds which possess a carbamoyl or N-alkylcarbamoyl substituent on the quinoline ring.

According to one aspect of the invention there is provided a quinoline derivative of the Formula I

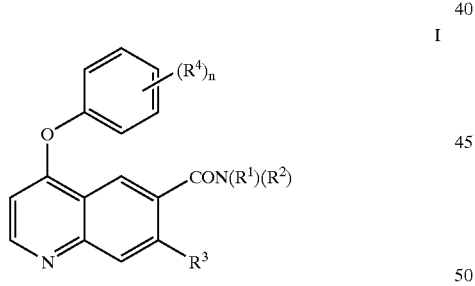

I wherein
n is 0, 1, 2 or 3 and each $R^4$, which may be the same or different, is halogeno, hydroxy, amino, nitro, trifluoromethyl, trifluoromethoxy, cyano, (1–6C)alkyl, (2–6C)alkenyl, (2–6C)alkynyl, (1–6C)alkoxy, (1–6C)alkylamino, di-[(1–6C)alkyl]amino, (2–6C)alkanoylamino, (1–6C)alkylthio, (1–6C)alkylsulphinyl, (1–6C)alkylsulphonyl, pyrrolidin-1-yl, piperidino, morpholino, piperazin-1-yl or 4-(1–6C)alkylpiperazin-1-yl, and any $CH_2$ or $CH_3$ group in a $R^4$ group optionally bears on each such $CH_2$ or $CH_3$ group a substituent selected from halogeno, hydroxy, amino, cyano, (1–6C)alkyl, (1–6C)alkoxy, (1–6C)alkylamino, di-[(1–6C)alkyl]amino and (2–6C)alkanoylamino, or $R^4$ is phenyl, phenoxy, anilino, N-(1–6C)alkylanilino, benzoyl, phenylthio, phenylsulphinyl, phenylsulphonyl, benzyl, pyridyl or pyridyloxy and the phenyl or pyridyl group in any of the 11 last-named substituents is optionally substituted with 1, 2 or 3 substituents, which may be the same or different, selected from halogeno, hydroxy, amino, nitro, trifluoromethyl, trifluoromethoxy, cyano, (1–6C)alkyl, (2–6C)alkenyl, (2–6C)alkynyl, (1–6C)alkoxy, (1–6C)alkylamino, di-[(1–6C)alkyl]amino and (2–6C)alkanoylamino, or $(R^4)_n$ is a (1–3C)alkylenedioxy substituent;

$R^1$ is hydrogen, (1–6C)alkyl, (2–6C)alkenyl or (2–6C)alkynyl;

$R^2$ is hydrogen, (1–6C)alkyl, (2–6C)alkenyl or (2–6C)alkynyl;

and wherein any $CH_2$ or $CH_3$ group in an $R^1$ or $R^2$ group optionally bears on each such $CH_2$ or $CH_3$ group a substituent selected from halogeno, hydroxy, amino, cyano, carbamoyl, sulphamoyl, (1–6C)alkoxy, (1–6C)alkylamino, di-[(1–6C)alkyl]amino, (2–6C)alkanoylamino, (1–6C)alkylthio, (1–6C)alkylsulphinyl, (1–6C)alkylsulphonyl, N-(1–6C)alkylcarbamoyl, N,N-di-[(1–6C)alkyl]carbamoyl, N-(1–6C)alkylsulphamoyl and N,N-di-[(1–6C)alkyl]sulphamoyl, or a substituent selected from aryl, aryloxy, arylamino, N-(1–6C)alkyl-arylamino, aryl-(1–6C)alkoxy, aryl-(1–6C)alkylamino, N-(1–6C)alkyl-aryl-(1–6C)alkylamino, aroylamino, N-arylcarbamoyl, aryl-(2–6C)alkanoylamino and N-[aryl-(1–6C)alkyl]carbamoyl, or a substituent selected from (3–7C)cycloalkyl, (3–7C)cycloalkyloxy, (3–7C)cycloalkylamino, N-(1–6C)alkyl-(3–7C)cycloalkylamino, (3–7C)cycloalkyl-(1–6C)alkoxy, (3–7C)cycloalkyl-(1–6C)alkylamino, N-(1–6C)alkyl-(3–7C)cycloalkyl-(1–6C)alkylamino, (3–7C)cycloalkylcarbonylamino, N-[(3–7C)cycloalkyl]carbamoyl, (3–7C)cycloalkyl-(2–6C)alkanoylamino and N-[(3–7C)cycloalkyl-(1–6C)alkyl]carbamoyl, or a substituent selected from heteroaryl, heteroaryloxy, heteroarylamino, N-(1–6C)alkyl-heteroarylamino, heteroaryl-(1–6C)alkoxy, heteroaryl-(1–6C)alkylamino, N-(1–6C)alkyl-heteroaryl-(1–6C)alkylamino, heteroarylcarbonylamino, N-heteroarylcarbamoyl, heteroaryl-(2–6C)alkanoylamino and N-[heteroaryl-(1–6C)alkyl]carbamoyl, or a substituent selected from heterocyclyl, heterocyclyloxy, heterocyclylamino, N-(1–6C)alkyl-heterocyclylamino, heterocyclyl-(1–6C)alkoxy, heterocyclyl-(1–6C)alkylamino, N-(1–6C)alkyl-heterocyclyl-(1–6C)alkylamino, heterocyclylcarbonylamino, N-heterocyclylcarbamoyl, heterocyclyl-(2–6C)alkanoylamino and N-[heterocyclyl-(1–6C)alkyl]carbamoyl, and wherein any aryl, (3–7C)cycloalkyl, heteroaryl or heterocyclyl group in a substituent on $R^1$ or $R^2$ optionally bears 1, 2 or 3 substituents, which may be the same or different, selected from halogeno, hydroxy, amino, nitro, trifluoromethyl, trifluoromethoxy, cyano, (1–6C)alkyl, (2–6C)alkenyl, (2–6C)alkynyl, (1–6C)alkoxy, (1–6C)alkylamino, di-[(1–6C)alkyl]amino and (2–6C)alkanoylamino and any (3–7C)cycloalkyl or heterocyclyl group on a $R^1$ or $R^2$ group optionally bears 1 or 2 oxo substituents; and $R^3$ is hydrogen, halogeno, hydroxy, amino, (1–6C)alkyl, (1–6C)alkoxy, (1–6C)alkylamino, di-[(1–6C)alkyl]amino or (2–6C)alkanoylamino;

or a pharmaceutically-acceptable salt thereof.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of Formula I defined above may exist in optically active or racemic forms by virtue of one or more asymmetric carbon atoms, the invention includes in its definition any such optically active or racemic form which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Suitable values for the generic radicals referred to above include those set out below.

A suitable value for a substituent on $R^1$ or $R^2$ when it is aryl or for the aryl group within a substituent on $R^1$ or $R^2$ is, for example, phenyl or naphthyl, preferably phenyl.

A suitable value for a substituent on $R^1$ or $R^2$ when it is (3–7C)cycloalkyl or for the (3–7C)cycloalkyl group within a substituent on $R^1$ or $R^2$ is, for example, cyclopropyl, cyclobutyl, cyclopentyl, cyclohexyl or cycloheptyl, preferably cyclopentyl or cyclohexyl. A suitable value for such a group which bears 1 or 2 oxo substituents is, for example, 2-oxocyclopentyl, 2-oxocyclohexyl or 4-oxocyclohexyl.

A suitable value for a substituent on $R^1$ or $R^2$ when it is heteroaryl or for the heteroaryl group within a substituent on $R_1$ or $R^2$ is, for example, an aromatic 5- or 6-membered monocyclic ring or a 9- or 10-membered bicyclic ring with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidazinyl, pyrazinyl, 1,3,5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl, preferably furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl or naphthyridinyl.

A suitable value for a substituent on $R_1$ or $R^2$ when it is heterocyclyl or for the heterocyclyl group within a substituent on $R^1$ and $R^2$ is, for example, a non-aromatic saturated or partially saturated 3 to 10 membered monocyclic or bicyclic ring with up to five heteroatoms selected from oxygen, nitrogen and sulphur, for example oxiranyl, oxetanyl, tetrahydrofuranyl, pyrrolinyl, pyrrolidinyl, imidazolinyl, imidazolidinyl, thiazolinyl, thiazolidinyl, pyrazolinyl, pyrazolidinyl, morpholinyl, piperidinyl, piperazinyl, homopiperazinyl, dihydropyridinyl, tetrahydropyridinyl, dihydropyrimidinyl, tetrahydropyrimidinyl, indolinyl, isoindolinyl, 2,3-dihydrobenzimidazolyl, 1,2,3,4-tetrahydroquinolinyl or chromanyl, preferably pyrrolidin-1-yl, imidazolidin-1-yl, thiazolidin-3-yl, morpholino, piperidino, piperazin-1-yl or homopiperazin-1-yl. A suitable value for such a group which bears 1 or 2 oxo substituents is, for example, 2-oxopyrrolidinyl, 2-oxoimidazolidinyl, 2-oxopiperidinyl, 2,5-dioxopyrrolidinyl, 2,4-dioxoimidazolidinyl, 2,5-dioxoimidazolidinyl, 2,4-dioxothiazolidinyl or 2,6-dioxopiperidinyl.

Suitable values for $R^1$, $R^2$, $R^3$ or $R^4$, or for various substituents on $R^1$, $R^2$ or $R^4$, or within a substituent on $R_1$ or $R^2$ include:

for halogeno fluoro, chloro, bromo and iodo;
for (1–6C)alkyl: methyl, ethyl, propyl, isopropyl and tert-butyl;
for (2–6C)alkenyl: vinyl, allyl and but-2-enyl;
for (2–6C)alkynyl: ethynyl, 2-propynyl and but-2-ynyl;
for (1–6C)alkoxy: methoxy, ethoxy, propoxy, isopropoxy and butoxy;
for (1–6C)alkylamino: methylamino, ethylamino, propylamino, isopropylamino and butylamino;
for di-[(1–6C)alkyl]amino: dimethylamino, diethylamino, N-ethyl-N-methylamino and diisopropylamino;
for (2–6C)alkanoylamino: acetamido and propionamido;
for (1–6C)alkylthio: methylthio, ethylthio and propylthio;
for (1–6C)alkylsulphinyl: methylsuiphinyl and ethylsulphinyl;
for (1–6C)alkylsulphonyl: methylsulphonyl and ethylsulphonyl;
for 4-(1–6C)alkylpiperazin-1-yl: 4-methylpiperazin-1-yl;
for N-(1–6C)alkylanilino: N-methylanilino and N-ethylanilino;
for pyridyl: 2-pyridyl, 3-pyridyl and 4-pyridyl;
for pyridyloxy: 2-pyridyloxy, 3-pyridyloxy and 4-pyridyloxy;
for N-(1–6C)alkylcarbamoyl: N-methylcarbamoyl and N-ethylcarbamoyl;
for N,N-di-[(1–6C)alkyl]carbamoyl: N,N-dimethylcarbamoyl and N,N-diethylcarbamoyl;
for N-(1–6C)alkylsulphamoyl: N-methylsulphamoyl and N-propylsulphamoyl; for N,N-di-[(1–6C)alkyl] sulphamoyl: N,N-dimethylsulphamoyl and N,N-dipropylsulphamoyl.

A suitable value for $(R^4)_n$ when it is (1–3C)alkylenedioxy is, for example, methylenedioxy or ethylenedioxy and the oxygen atoms thereof occupy adjacent positions on the phenyl ring.

When, as defined hereinbefore, any $CH_2$ or $CH_3$ group in an $R^4$ group optionally bears on each such $CH_2$ or $CH_3$ group a substituent as defined hereinbefore, suitable $R^4$ groups so formed include, for example, a (1–6C)alkylamino-(1–6C)alkoxy group such as 2-methylaminoethoxy and 3-methylaminopropoxy, a di-[(1–6C)alkyl]amino-(1–6C) alkoxy group such as 2-dimethylaminoethoxy and 3-dimethylaminopropoxy, a (1–6C)alkylamino-(1–6C) alkylamino group such as 2-methylaminoethylamino and 3-methylaminopropylamino, a di-[(1–6C)alkyl]amino-(1–6C)alkylamino group such as 2-dimethylaminoethylamino and 3-dimethylaminopropylamino, and a (1–6C)alkoxy-(1–6C) alkyl group such as 2-methoxyethyl.

Suitable values for substituents on $R^1$ or $R^2$ include:
for N-(1–6C)alkyl-heteroarylamino: N-methylheteroarylamino;
for heteroaryl-(1–6C)alkoxy: heteroarylmethoxy and 2-heteroarylethoxy;
for heteroaryl-(1–6C)alkylamino: heteroarylmethylamino, 2-heteroarylethylamino and 3-heteroarylpropylamino;
for N-(1–6C)alkyl-heteroaryl-(1–6C)alkylamino: N-methylheteroarylmetlhylamino and N-methyl-2-heteroarylethylamino;
for heteroaryl-(2–6C)alkanoylamino: heteroarylacetamido and 3-heteroarylpropionamido;
for N-[heteroaryl-(1–6C)alkyl]carbamoyl: N-heteroarylmethylcarbamoyl and N-(2-heteroarylethyl) carbamoyl.

The invention comprises corresponding suitable values for substituents on $R^1$ or $R^2$ when, for example, rather than a heteroaryl-(1–6C)alkoxy group, an aryl-(1–6C)alkoxy, (3–7C)cycloalkyl-(1–6C)alkoxy or heterocyclyl-(1–6C) alkoxy group is present.

When, as defined hereinbefore, any $CH_2$ or $CH_3$ group in an $R^1$ or $R^2$ group optionally bears on each such $CH_2$ or $CH_3$ group a substituent as defined hereinbefore, suitable $R^1$ and $R^2$ groups so formed include, for example, aryl-(1–6C)alkyl groups such as 2-phenethyl and 3-phenylpropyl, aroylamino-(1–6C)alkyl groups such as 3-benzamidopropyl, (3–7C)cyclopropyl-(1–6C)alkyl groups such as 3-cyclopentylpropyl, N-[(3–7C)cycloalkyl]-carbamoyl-(1–6C)alkyl groups such as 3-(N-cyclohexylcarbamoyl) propyl, heteroaryl-(1–6C)alkyl groups such as 2-(2-pyridyl) ethyl, heteroarylcarbonylamino-(1–6C)alkyl groups such as 3-(2-pyridylcarbonylamino)propyl, heterocyclyl-(1–6C) alkyl groups such as 2-pyrrolidin-1-ylethyl, 3-morpholinopropyl and 2-hydroxy-3-piperidinopropyl, substituted (1–6C)alkoxy-(1–6C)alkyl groups such as 2-methoxyethyl, substituted (1–6C)alkylamino-(1–6C)alkyl groups such as 2-methylaminoethyl, substituted di-[(1–6C) alkyl]amino-(1–6C)alkyl groups such as 2-dimethylaminoethyl and substituted (1–6C)alkylthio-(1–6C)alkyl groups such as 2-methylthioethyl.

A suitable pharmaceutically-acceptable salt of a compound of the Formula I is, for example, an acid-addition salt of a compound of the Formula I which is sufficiently basic, for example an acid-addition salt with an inorganic or organic acid such as hydrochloric, hydrobromic, sulphuric, trifluoroacetic, citric or maleic acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

According to a further aspect of the invention there is provided a quinoline derivative of the Formula I

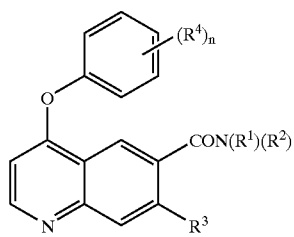

I wherein
n is 0, 1, 2 or 3 and $R^4$ is halogeno, hydroxy, amino, nitro, trifluoromethyl, trifluoromethoxy, cyano, (1–6C)alkyl, (2–6C)alkenyl, (2–6C)alkynyl, (1–6C)alkoxy, (1–6C) alkylamino, di-[(1–6C)alkyl]amino, (2–6C) alkanoylamino, phenyl, phenoxy, anilino, phenylthio, phenylsulphinyl, phenylsulphonyl or benzyl and the phenyl group in any of the 7 last-named substituents is optionally substituted with 1, 2 or 3 substituents selected from halogeno, hydroxy, amino, nitro, trifluoromethyl, trifluoromethoxy, cyano, (1–6C)alkyl, (2–6C)alkenyl, (2–6C)alkynyl, (1–6C)alkoxy, (1–6C) alkylamino, di-[(1–6C)alkyl]amino and (2–6C) alkanoylamino, or $(R^4)_n$ is a (1–3C)alkylenedioxy substituent;

$R^1$ is hydrogen, (1–6C)alkyl, (2–6C)alkenyl or (2–6C) alkynyl;

$R^2$ is hydrogen, (1–6C)alkyl, (2–6C)alkenyl or (2–6C) alkynyl;

and wherein any $CH_2$ or $CH_3$ group in an $R^1$ or $R^2$ group optionally bears on each such $CH_2$ or $CH_3$ group a substituent selected from halogeno, hydroxy, amino, cyano, (1–6C)alkoxy, (1–6C)alkylamino, di-[(1–6C) alkyl]amino and (2–6C)alkanoylamino, or a substituent selected from aryl, aryloxy, arylamino, N-(1–6C)alkyl-arylamino, aryl-(1–6C)alkoxy, aryl-(1–6C)alkylamino, N-(1–6C)alkyl-aryl-(1–6C)alkylamino, aroylamino, N-arylcarbamoyl, aryl-(2–6C)alkanoylamino and N-[aryl-(1–6C)alkyl]carbamoyl, or a substituent selected from (3–7C)cycloalkyl, (3–7C)cycloalkyloxy, (3–7C)cycloalkylamino, N-(1–6C)alkyl-(3–7C) cycloalkylamino, (3–7C)cycloalkyl-(1–6C)alkoxy, (3–7C)cycloalkyl-(1–6C)alkylamino, N-(1–6C)alkyl-(3–7C)cycloalkyl-(1–6C)alkylamino, (3–7C) cycloalkylcarbonylamino, N-[(3–7C)cycloalkyl] carbamoyl, (3–7C)cycloalkyl-(2–6C)alkanoylamino and N-[(3–7C)cycloalkyl-(1–6C)alkyl]carbamoyl, or a substituent selected from heteroaryl, heteroaryloxy, heteroarylamino, N-(1–6C)alkyl-heteroarylamino, heteroaryl-(1–6C)alkoxy, heteroaryl-(1–6C) alkylamino, N-(1–6C)alkyl-heteroaryl-(1–6C) alkylamino, heteroarylcarbonylamino, N-heteroarylcarbamoyl, heteroaryl-(2–6C) alkanoylamino and N-[heteroaryl-(1–6C)alkyl] carbamoyl, or a substituent selected from heterocyclyl, heterocyclyloxy, heterocyclylamino, N-(1–6C)alkyl-heterocyclylamino, heterocyclyl-(1–6C)alkoxy, heterocyclyl-(1–6C)alkylamino, N-(1–6C)alkyl-heterocyclyl-(1–6C)alkylamino, heterocyclylcarbonylamino, N-heterocyclylcarbamoyl, heterocyclyl-(2–6C)alkanoylamino and N-[heterocyclyl-(1–6C)alkyl]carbamoyl, and wherein any aryl, (3–7C)cycloalkyl, heteroaryl or heterocyclyl group in a substituent on $R^1$ or $R^2$ optionally bears 1, 2 or 3 substituents selected from halogeno, hydroxy, amino, nitro, trifluoromethyl, trifluoromethoxy, cyano, (1–6C)alkyl, (2–6C)alkenyl, (2–6C)alkynyl, (1–6C) alkoxy, (1–6C)alkylamino, di-[(1–6C)alkyl]amino, and (2–6C)alkanoylamino and any (3–7C)cycloalkyl or heterocyclyl group on a $R^1$ or $R^2$ group optionally bears 1 or 2 oxo substituents; and $R^3$ is hydrogen, halogeno, hydroxy, amino, (1–6C)alkyl, (1–6C)alkoxy, (1–6C)alkylamino, di-[(1–6C)alkyl] amino or (2–6C)alkanoylamino;

or a pharmaceutically-acceptable salt thereof.

Particular novel compounds of the invention include, for example, quinoline derivatives of the Formula I, or pharmaceutically-acceptable salts thereof, wherein, unless otherwise stated, each of n, $R^1$, $R^2$, $R^3$ and $R^4$ has any of the meanings defined hereinbefore or in this section concerning particular compounds of the invention:

(a) when $R^2$ is hydrogen, $R^1$ has one of the meanings defined hereinbefore other than hydrogen;

(b) $R^2$ is hydrogen and $R^1$ is (1–6C)alkyl wherein 1 or 2 $CH_2$ or $CH_3$ groups bears a substituent as defined hereinbefore;

(c) $R^2$ is hydrogen and $R^1$ is (1–6C)alkyl which bears 1 or 2 substituents selected from hydroxy, amino, cyano, (1–6C)alkoxy, (1–6C)alkylamino, di-[(1–6C)alkyl] amino, (2–6C)alkanoylamino, phenyl, phenoxy, phenyl-(1–6C)alkoxy, benzamido, N-phenylcarbamoyl, (3–7C)cycloalkyl, (3–7C) cycloalkyloxy, (3–7C)cycloalkyl-(1–6C)alkoxy, (3–7C)cycloalkylcarbonylamino, N-[(3–7C)cycloalkyl]carbamoyl, heteroaryl, heteroaryloxy, heteroaryl-(1–6C)alkoxy, heteroarylcarbonylamino, N-heteroarylcarbamoyl, heterocyclyl, heterocyclyloxy, heterocyclyl-(1–6C)alkoxy, heterocyclylcarbonylamino and N-heterocyclylcarbamoyl and wherein any phenyl, heteroaryl or heterocyclyl group in a $R^1$ substituent optionally bears 1 or 2 substituents selected from halogeno, hydroxy, amino, trifluoromethyl, cyano, (1–6C)alkyl, (1–6C)alkoxy, (1–6C)alkylamino, di-[(1–6C)alkyl]amino and (2–6C)alkanoylamino and wherein any (3–7C)cycloalkyl or heterocyclyl group in a $R^1$ substituent optionally bears 1 or 2 oxo substituents;

(d) $R^2$ is hydrogen and $R^1$ is (1–6C)alkyl which bears 1 or 2 substituents selected from hydroxy, amino, cyano, (1–6C)alkoxy, (1–6C)alkylamino, di-[(1–6C)alkyl]amino, (2–6C)alkanoylamino, phenyl, furyl, thienyl, pyrrolyl, imidazolyl, pyrazolyl, pyridyl, pyrimidinyl, furylcarbonylamino, thienylcarbonylamino, pyridylcarbonylamino, pyrrolidinyl, imidazolidinyl, morpholinyl, piperidinyl, piperazinyl and homopiperazinyl and wherein any of the 17 last-named substituents on $R^1$ optionally bears 1 or 2 further substituents selected from halogeno, hydroxy, amino, trifluoromethyl, cyano, (1–6C)alkyl, (1–6C)alkoxy, (1–6C)alkylamino, di-[(1–6C)alkyl]amino and (2–6C)alkanoylamino and wherein any of the 6 heterocyclic substituents on $R^1$ (from pyrrolidinyl to homopiperazinyl) optionally bears 1 or 2 oxo substituents; and (e) $R^3$ is (1–6C)alkoxy.

A preferred compound of the invention is a quinoline derivative of the Formula I wherein n is 1, 2 or 3 and each $R^4$ group is independently selected from fluoro, chloro, bromo, hydroxy, amino, trifluoromethyl, methyl, methoxy, methylamino, dimethylamino, acetamido, phenyl and phenoxy and wherein said 2 last-named substituents optionally bear 1, 2 or 3 substituents selected from fluoro, chloro, bromo, methyl and methoxy;

$R^2$ is hydrogen;

$R^1$ is ethyl, propyl or butyl which bears 1 or 2 substituents selected from hydroxy, amino, cyano, methoxy, ethoxy, methylamino, ethylamino, dimethylamino, diethylamino, acetamido, phenyl, imidazolyl, pyridyl, pyrrolidinyl, imidazolidinyl, morpholinyl, piperidinyl and piperazinyl and wherein any of the 8 last-named substituents on $R^1$ optionally bears 1 or 2 further substituents selected from fluoro, chloro, bromo, hydroxy, amino, trifluoromethyl, cyano, methyl, methoxy, methylamino, dimethylamino and acetamido and wherein any of the pyrrolidinyl, imidazolidinyl, morpholinyl, piperidinyl and piperazinyl substituents on $R^1$ optionally bears 1 or 2 oxo substituents; and $R^3$ is methoxy;

or a pharmaceutically-acceptable salt thereof.

A further preferred compound of the invention is a quinoline derivative of the Formula I wherein n is 1, 2 or 3 and each $R^4$ group is independently selected from fluoro, chloro, bromo, hydroxy, amino, trifluoromethyl, cyano, methyl, ethyl, methoxy, ethoxy, methylamino, ethylamino, propylamino, butylamino, dimethylamino, diethylamino, acetamido, methylthio, piperidin-1-yl, piperidino, morpholino, piperazin-1-yl, 4-methylpiperazin-1-yl, phenyl, phenoxy, anilino, N-methylanilino, benzoyl, phenylthio, benzyl, 4-pyridyl and 4-pyridyloxy;

$R^2$ is hydrogen;

$R^1$ is ethyl, propyl or butyl which bears a substituent selected from hydroxy, amino, methoxy, methylamino, dimethylamino, acetamido, methylthio, methylsulphinyl, methylsulphonyl, N-methylcarbamoyl, N,N-dimethylcarbamoyl, N-methylsulphamoyl, N-ethylsulphamoyl, N-propylsulphamoyl, N,N-dimethylsulphamoyl, 4-chlorophenyl, 4-aminophenyl, 4-methoxyphenyl, 1-imidazolyl, 2-imidazolyl, 2-pyridyl, pyrrolidin-1-yl, 2-oxopyrrolidin-1-yl, 2-oxoimidazolidin-1-yl, 2,4-dioxoimidazolidin-1-yl, 5-methyl-2,4-dioxothiazolidin-3-yl, piperidino, 2,6-dioxopiperidin-1-yl, morpholino, piperazin-1-yl and 4-methylpiperazin-1-yl;

and $R^3$ is methoxy;

or a pharmaceutically-acceptable salt thereof.

A further preferred compound of the invention is a quinoline derivative of the Formula I wherein n is 1 or 2 and each $R^4$ group is independently selected from fluoro, chloro, dimethylamino, acetamido, phenyl and phenoxy;

$R^2$ is hydrogen;

$R^1$ is ethyl or propyl which bears a substituent selected from 4-chlorophenyl, 4-aminophenyl, 4-methoxyphenyl, 2-pyridyl, 2-oxoimidazolidin-1-yl and morpholino; and $R^3$ is methoxy;

or a pharmaceutically-acceptable salt thereof

A particular preferred compound of the invention is, for example, a quinoline derivative of the Formula I selected from:

4-(4-chloro-2-fluorophenoxy)-7-methoxy-N-(3-morpholinopropyl)quinoline-6-carboxamide, 4-(3,4-dichlorophenoxy)-7-methoxy-N-(3-morpholinopropyl)quinoline-6-carboxamide, 4-(4-chloro-2-fluorophenoxy)-N-[2-(2-oxoimidazolidin-1-yl)ethyl]-7-methoxyquinoline-6-carboxamide and 7-methoxy-N-(3-morpholinopropyl)-4-(4-phenoxyphenoxy)quinoline-6-carboxamide;

or a pharmaceutically-acceptable salt thereof.

A quinoline derivative of the Formula I, or a pharmaceutically-acceptable salt thereof, may be prepared by any process known to be applicable to the preparation of chemically-related compounds. Such processes, when used to prepare a quinoline derivative of the Formula I are provided as a further feature of the invention and are illustrated by the following representative process variants in which, unless otherwise stated, $R^1$, $R^2$, $R^3$, $R^4$ and n have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

(a) The reaction, conveniently in the presence of a suitable base, of a quinoline of the Formula II

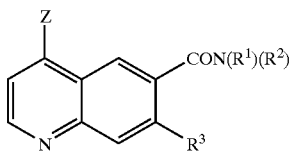

wherein Z is a displaceable group and $R^1$, $R^2$, $R^3$ and m have any of the meanings defined hereinbefore except that any functional group is protected if necessary, with a phenol of the Formula III

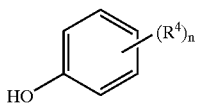

wherein $R^4$ and n have any of the meanings defined hereinbefore except that any functional group is protected if necessary, whereafter any protecting group that is present is removed by conventional means.

A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate, alkoxide or hydroxide, for example sodium carbonate, potassium carbonate, calcium carbonate, sodium ethoxide, potassium tert-butoxide, sodium hydroxide or potassium hydroxide, or, for example, an alkali metal hydride, for example sodium hydride or potassium hydride, or an organometallic base such as an alkyl-lithium, for example n-butyl-lithium or a dialkylamino-lithium, for example lithium di-isopropylamide.

A suitable displaceable group Z is, for example, a halogeno, alkoxy, aryloxy or sulphonyloxy group, for example a chloro, bromo, methoxy, phenoxy, methanesulphonyloxy or toluene-4-sulphonyloxy group. The reaction is conveniently carried out in the presence of a suitable inert solvent or diluent, for example an alkanol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such an N,N-dimethylformamide, N,N-dimethylacetamide, N-methylpyrrolidin-2-one or dimethylsulphoxide. The reaction is conveniently carried out at a temperature in the range, for example, 10 to 250° C., preferably in the range 50 to 150° C.

The quinoline derivative of the Formula I may be obtained from this process in the form of the free base or alternatively it may be obtained in the form of a salt with the acid of the formula H-Z wherein Z has the meaning defined hereinbefore. When it is desired to obtain the free base from the salt, the salt may be treated with a suitable base, for example, an organic amine base such as, for example, pyridine, 2,6-lutidine, collidine, 4-dimethylaminopyridine, triethylamine, morpholine, N-methylmorpholine or 1,8-diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1–20 carbon atoms). Examples of carboxy protecting groups include straight or branched chain (1–12C) alkyl groups (for example isopropyl, and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower alkyl groups (for example 1-methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl) silyl groups (for example trimethylsilyl and tert-butyldimethylsilyl); tri(lower alkyl)silyl-lower alkyl groups (for example trimethylsilylethyl); and (2–6C)alkenyl groups (for example allyl). Methods particularly appropriate for the removal of carboxyl protecting groups include for example acid-, base-, metal- or enzymically-catalysed hydrolysis.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxybenzyl, and triphenylmethyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl, hydrogenation for groups such as benzyl and photolytically for groups such as 2-nitrobenzyloxycarbonyl.

The reader is referred to Advanced Organic Chemistry, 4th Edition, by J. March, published by John Wiley & Sons 1992, for general guidance on reaction conditions and reagents and to Protective Groups in Organic Synthesis, $2^{nd}$ Edition, by T. Green et al., also published by John Wiley & Son, for general guidance on protecting groups.

The quinoline of the Formula II may be prepared by, for example, the reaction of a carboxylic acid of the Formula IV, or a reactive derivative thereof,

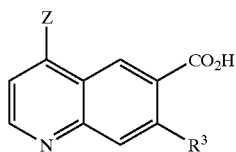

IV wherein Z and $R^3$ have any of the meanings defined hereinbefore except that any functional group is protected if necessary, with an amine of the Formula V

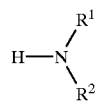

V wherein $R^1$ and $R^2$ have any of the meanings defined hereinbefore except that any functional group is protected if necessary, whereafter any protecting group that is present may be removed by conventional means.

A suitable reactive derivative of a carboxylic acid of the Formula IV is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol, an ester formed by the reaction of the acid and an ester such as pentafluorophenyl trifluoroacetate or an ester formed by the reaction of the acid and an alcohol such as N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide or 1-(3-dimethylaminopropyl)-3-ethylcarbodiimide.

The reaction is conveniently carried out in the presence of a suitable base as defined hereinbefore and in the presence of a suitable inert solvent or diluent as defined hereinbefore.

Typically a carbodiimide coupling reagent is used in the presence of an organic solvent (preferably an anhydrous polar aprotic organic solvent) at a non-extreme temperature, for example in the region −10 to 40° C., typically at ambient temperature of about 20° C.

The quinoline of the Formula IV may be prepared by standard procedures of organic chemistry such as the relevant procedures illustrated in the accompanying Examples. For example, a quinolone of the Formula VI

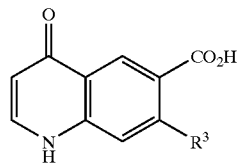

VI wherein $R^3$ has any of the meanings defined hereinbefore except that any functional group is protected if necessary and wherein the carboxy group at the 6-position is protected, for example as a lower alkyl (for example ethyl) ester, may be reacted with a halogenating agent whereafter the carboxy protecting group at the 6-position is removed by conventional means and any other protecting group that is present may be removed by conventional means to form a benzoic acid derivative of the Formula IV wherein Z is a halogeno group.

Convenient halogenating agents include, for example, inorganic acid halides, for example thionyl chloride, phosphorus trichloride, phosphorus tribromide, phosphoryl chloride and phosphorus pentachloride. The reaction is conveniently carried out in the presence of an excess of the halogenating agent as a solvent or diluent or in the presence of a separate solvent or diluent such as, for example, a halogenated solvent such as methylene chloride, chloroform or carbon tetrachloride. The reaction is conveniently carried out at a temperature in the range, for example, 10 to 150° C., preferably in the range 40 to 100° C.

The quinolone of the Formula VI may be prepared by standard procedures of organic chemistry such as those relevant procedures illustrated in the accompanying Examples.

(b) The reaction of a carboxylic acid of the Formula VII, or a reactive derivative thereof as defined hereinbefore,

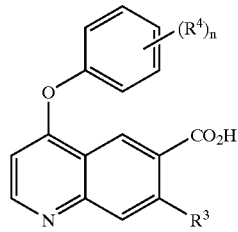

VII wherein $R^3$, $R^4$ and n have any of the meanings defined hereinbefore except that any functional group is protected if necessary, with an amine of the Formula V

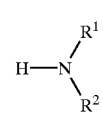

V wherein $R^1$ and $R^2$ have any of the meanings defined hereinbefore except that any functional group is protected if necessary, whereafter any protecting group that is present is removed by conventional means.

The reaction is conveniently carried out in the presence of a suitable base as defined hereinbefore and in the presence of a suitable inert solvent or diluent as defined hereinbefore. Typically a carbodiimide coupling reagent is used, preferably also in the presence of an ester-forming alcohol such as N-hydroxybenzotriazole, and the reaction is carried out at a temperature at or near ambient temperature of about 20° C.

The carboxylic acid of the Formula VII may be prepared by, for example, the reaction, conveniently in the presence of a suitable base as defined hereinbefore, of a quinoline of the Formula IV

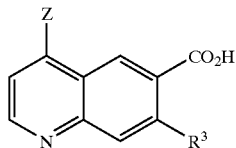

IV wherein Z is a displaceable group as defined hereinbefore and $R^3$ has any of the meanings defined hereinbefore except that any functional group is protected if necessary and wherein the carboxy group at the 6-position may be protected, for example as a lower alkyl (for example ethyl) ester, with a phenol of the Formula III

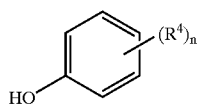

III wherein $R^4$ and n have any of the meanings defined hereinbefore except that any functional group is protected if necessary, whereafter any protecting group that is present may be removed by conventional means.

The reaction is conveniently carried out in the presence of a suitable inert solvent or diluent or defined hereinbefore and at a temperature in the range, for example, 10 to 250° C., preferably in the range 50 to 150° C.

(c) For the preparation of those compounds of the Formula I wherein $R^4$ is an amino, (1–6C)alkylamino, di-[(1–6C)alkyl]amino, anilino or N-(1–6C)alkylanilino group, the reaction of a compound of the Formula VIII wherein $R^1$, $R^2$ and $R^3$ have any of the meanings defined hereinbefore except that any functional group is protected if necessary and Z is a displaceable group as defined hereinbefore,

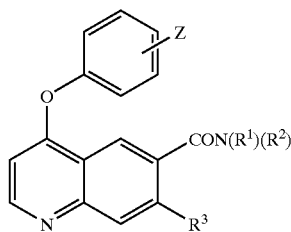

VIII with an amine or aniline as appropriate whereafter any protecting group that is present is removed by conventional means.

The reaction is conveniently carried out in the presence of a suitable base as defined hereinbefore and in the presence of a suitable inert solvent or diluent as defined hereinbefore. Typically the reaction is carried out at a temperature in the range, for example, 10 to 250° C., preferably in the range 50 to 100° C.

When, for example, in the compound of the Formula VIII the displaceable group Z is a halogeno group, that necessary starting material can be prepared using either of the processes of process variants (a) or (b) as defined hereinbefore.

When a pharmaceutically-acceptable salt of a quinoline derivative of the Formula I is required, for example an acid-addition salt, it may be obtained by, for example, reaction of said quinoline derivative with a suitable acid using a conventional procedure.

Biological Assays

The following assays can be used to measure the effects of the compounds of the present invention as $p56^{lck}$ inhibitors, as inhibitors of T cell activation, as inhibitors of cytokine production in mice and as inhibitors of transplant rejection.

(a) In vitro Enzyme Assay

The ability of test compounds to inhibit phosphorylation by the enzyme $p56^{lck}$ of a tyrosine-containing polypeptide substrate was assessed using a conventional Elisa assay.

The following conventional procedure was used to obtain $p56^{lck}$ enzyme. An EcoR1/Not1 fragment containing the entire coding sequence of $p56^{lck}$ was generated by the technique of polymerase chain reaction (PCR) from Incyte clone No. 2829606. A 6-His tag was added to the sequence at the N-terminus during the PCR stage. Conventional sequence analysis identified a number of changes compared to the published sequence and these were found also to have been present in the original Incyte template. To achieve expression of the enzyme, the PCR fragment was inserted downstream of the polyhedrin promotor of pFASTBAC1 (Life Technologies Limited, Paisley, UK, Catalogue No. 10360-014). A recombinant Baculovirus was constructed using the Bac-to-Bac system (Life Technologies Limited). High Five insect cells (Invitrogen BV, PO Box 2312, 9704 CH Groningen, The Netherlands, Catalogue No. B855-02) were infected with the recombinant Baculovirus at a multiplicity of infection of 1 and incubated for 48 hours. The cells were harvested. Groups of $1.6 \times 10^9$ cells were lysed by incubation in 20 mM Hepes pH7.5 buffer containing 10% glycerol, 1% Triton-X-100, magnesium chloride (1.5 mM), ethylene glycol bis(β-aminoethyl ether N,N,N',N'-tetraacetic acid) (EGTA, 1 mM), sodium vanadate (1 mM), sodium fluoride (10 mM), imidazole (5 mM), sodium chloride (150 mM), phenylmethanesulphonyl fluoride (0.1 mM), pepstatin (1 μg/ml) and leupeptin (1 μg/ml). A soluble fraction was obtained by centrifugation and 6-His-$p56^{lck}$ was purified by column chromatography on a 1 ml Ni-NTA agarose column (Qiagen Limited, Crawley, West Sussex, UK). The protein was eluted using the above-mentioned buffer except that imidazole (100 mM) was also present. The $p56^{lck}$ enzyme so obtained was stored at −80° C.

Substrate solution [100 μl of a 2 μg/ml solution of the polyamino acid Poly(Glu, Ala, Tyr) 6:3:1 (Sigma Catalogue No. P3899) in phosphate buffered saline (PBS)] was added to each well of a Nunc 96-well immunoplate (Catalogue No. 439454) and the plate was sealed and stored at 4° C. for 16 hours. The excess of substrate solution was discarded, the substrate-coated wells were washed with Hepes pH7.4 buffer(50 mM, 300 μl) and blotted dry. Each test compound was dissolved in DMSO and diluted to give a series of dilutions (from 100 μM to 0.001 μM) of the compound in a 10:1 mixture of water and DMSO. Portions (25 μl) of each dilution of test compound were transferred to the 96-well assay plate. Aliquots (25 μl) of a 10:1 mixture of water and DMSO were added followed by aliquots (25 μl) of a mixture of adenosine triphosphate (ATP; 24 μl of a 1 mM aqueous solution) and manganese chloride (3 ml of a 40 mM aqueous solution).

$p56^{lck}$ enzyme (0.3 μl of a 0.5 mg/ml stock solution) was diluted in a mixture of Hepes pH 7.4 buffer (200 mM, 3 ml), sodium orthovanadate (2 mM, 0.6 ml), 1% Triton X-100 (0.6 ml), dithiothreitol (25 mM, 48 µl) and distilled water (1.8 ml). Aliquots (50 µl) of the resultant solution were transferred to each well in the assay plate and the plate was incubated at ambient temperature for 8 minutes. The wells were washed sequentially with two aliquots (300 µl) of phosphate-buffered saline (PBS) containing 0.1% Tween 20 (hereinafter PBS/T).

Aliquots (100 µl) were added to each well of a mixture of antiphosphotyrosine-4G10 monoclonal IgG2 bk antibody (UBI Catalogue No. 05-321; 30 µl of a 50 µg/ml solution of the antibody in PBS/T), PBS/T (11 ml) and bovine serum albumin (BSA; Sigma Catalogue No. A6793; 55 mg) and the plate was incubated at ambient temperature for 1 hour. The wells were washed sequentially with two aliquots (300 µl) of PBS/T and blotted dry. Aliquots (100 µl) were added to each well of a mixture of sheep anti-mouse IgG-peroxidase antibody (Amersham Catalogue No. NXA931; 20 µl), PBS/T (11 ml) and BSA (55 mg) and the plate was incubated at ambient temperature for 1 hour. The wells were washed sequentially with two aliquots (300 µl) of PBS/T and blotted dry.

Aliquots (100 µl) were added to each well of an ABTS solution [prepared by adding an 2,2'-azinobis(3-ethylbenzothiazolinesulphonic acid) (ABTS) tablet (50 mg; Boehringer Catalogue No, 1204521) to a mixture (50 mM) of phosphate-citrate pH5.0 buffer and 0.03% sodium perborate (obtained by adding a PCSB capsule (Sigma Catalogue No. P-4922) to distilled water (100 ml))]. The plate was incubated at ambient temperature for 1.5 hours and the absorbance at 405 nm was determined.

The extent of inhibition of the phosphorylation reaction at a range of concentrations of each test compound was determined and an $IC_{50}$ value was calculated.

(b) In vitro T Cell Proliferation Assays

The ability of test compounds to inhibit T cell proliferation was assessed by using human peripheral blood mononuclear cells and stimulation of the T cells by way of the T cell receptor or other than by way of the T cell receptor.

Peripheral blood mononuclear cells (PBMC) were isolated from heparinised (10 units/ml heparin) human blood by density centrifugation (Lymphoprep™; Nycomed) spinning initially at 2000 rpm at ambient temperature for 20 minutes. Cells at the interphase were transferred to clean tubes, diluted 1:1 with RPMI 1640 medium (Gibco) and spun at 2000 rpm at ambient temperature for 10 minutes. The cell pellet was resuspended in RPMI 1640 medium and spun at 1400 rpm at ambient temperature for 10 minutes. The cell pellet was resuspended in RPMI 1640 medium and spun at 900 rpm at ambient temperature for 10 minutes to remove platelets. The prepared mononuclear cells were resuspended in an assay medium comprising RPMI 1640 culture medium supplemented with 50 units/ml penicillin, 50 µg/ml streptomycin, 1 mM glutamine and 10% heat-inactivated human AB serum.

Test compounds were solubilised in DMSO at a concentration of 10 mM and diluted 1:83.3 in assay medium. Aliquots (75 µl) were added to each well of a 96 well flat-bottomed tissue culture plate and subsequently serial 1 to 3 dilutions were made into assay medium giving final test concentrations in the range 0.1 to 30 µM. Control wells contained assay medium (50 µl) containing 1.2% DMSO. PBMCs (100 µl of a suspension of $2 \times 10^6$ cells/ml in assay medium) were added to each well and incubated for 1 hour at 37° C. in a humidified (5%$CO_2$/95% air) incubator.

The extent of inhibition of T cell proliferation at a range of concentrations of each test compound was determined and an $IC_{50}$ value was calculated.

(b)(i) T Cell Receptor Stimulation

Aliquots (50 µl) of the T cell receptor stimulatory anti-CD3 antibody (Pharmingen Catalogue No. 30100D; 40 ng/ml in assay medium) were added to each well and the cells were incubated for 24 hours at 37° C. in a humidified (5%$CO_2$/95% air) incubator. Tritiated thymidine (1 µCi per well) was added and the cells were incubated for up to a further 24 hours at 37° C. The cells were harvested onto a filter mat and radioactivity was counted using a Wallac 1450 Microbeta Plus liquid scintillation counter.

(b)(ii) Non T Cell Receptor Stimulation

Aliquots (50 µl) of a mixture of the cell stimulants PMA (phorbol-12-myristate-13-acetate, Sigma Catalogue No. P8139; 40 ng/ml) and Ionomycin (Sigma Catalogue No. I0684; 1.2 µM) were added to each well and the cells were incubated and analysed as described in paragraph (b)(i).

(c) In vivo Skin Graft Rejection Test

The ability of test compounds to inhibit rodent skin allograft rejection was assessed using analogous procedures to those disclosed by J. Magae et al., *Cellular Immunology*, 1996, 173, 276–281 and R. Tsuji et al., *J. Antibiot.*, 1992, 45, 1295 to assess the effect of cyclosporin A on T cell properties in vivo.

(d) Test as Anti-arthritic Agent

Activity of a test compound as an anti-arthritic agent was assessed as follows. Acid soluble native type II collagen has been shown to be arthritogenic in rats causing polyarthritis when administered in Freunds incomplete adjuvant by (D. E. Trentham et al. *J. Exp. Med.*, 1977, 146, 857). This is now known as collagen-induced arthritis (CIA) and similar conditions can be induced in mice and primates. CIA in DBA/1 mice as described by R. O. Williams et al., *Proc Natl. Acad Sci.*, 1992, 89, 9784 and Immunology, 1995, 84, 433 is a tertiary model which can be used to demonstrate the anti-arthritic activity of a test compound.

Although the pharmacological properties of the compounds of the Formula I vary with structural change as expected, in general activity possessed by compounds of the Formula I may be demonstrated at the following concentrations or doses in one or more of the above tests (a), (b), (c) and (d):

Test (a):—$IC_{50}$ in the range, for example, 0.001–10 µM;

Test (b)(i):—$IC_{50}$ in the range, for example, 0.1–20 µM;

Test (b)(ii):—$IC_{50}$ in the range, for example, 5–>30 µM;

Test (c):—activity in the range, for example, 1–100 mg/kg;

Test (d):—activity in the range, for example, 1–100 mg/kg;.

No physiologically-unacceptable toxicity was observed at the effective dose for compounds tested of the present invention.

By way of example, 4-(4-chloro-2-fluorophenoxy)-7-methoxy-N-(3-morpholinopropyl)quinoline-6-carboxamide (Example 1) has an $IC_{50}$ of approximately 0.03 µM in Test (a); an $IC_{50}$ of approximately 0.7 µM in Test (b)(i) and an $IC_{50}$ of approximately 18 µM in Test (b)(ii).

According to a further aspect of the invention there is provided a pharmaceutical composition which comprises a quinoline derivative of the Formula I, or a pharmaceutically-acceptable salt thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.5 mg/kg to 75 mg/kg body weight is received, given if required in divided doses. In general lower doses will be administered when a parenteral route is employed. Thus, for example, for intravenous administration, a dose in the range, for example, 0.5 mg/kg to 30 mg/kg body weight will generally be used. Similarly, for administration by inhalation, a dose in the range, for example, 0.5 mg/kg to 25 mg/kg body weight will be used. Oral administration is however preferred, particularly in tablet form. Typically, unit dosage forms will contain about 0.5 mg to 0.5 g of a compound of this invention.

According to a further aspect of the invention there is provided a quinoline derivative of the Formula I, or a pharmaceutically-acceptable salt thereof, as defined hereinbefore for use in a method of treatment of the human or animal body by therapy.

We have found that the compounds of the present invention are of use in the prevention or treatment of autoimmune diseases or medical conditions, for example T cell mediated disease such as transplant rejection, rheumatoid arthritis or multiple sclerosis. We have further found that these effects are believed to arise by virtue of inhibition of one or more of the multiple tyrosine-specific protein kinases which are involved in the early signal transduction steps which lead to full T cell activation, for example by way of inhibition of the enzyme $p56^{lck}$. Accordingly the compounds of the present invention are expected to be useful in the prevention or treatment of T cell mediated diseases or medical conditions. In particular the compounds of the present invention are expected to be useful in the prevention or treatment of those pathological conditions which are sensitive to inhibition of one or more of the multiple tyrosine-specific protein kinases which are involved in the early signal transduction steps which lead to T cell activation, for example by way of inhibition of $p56^{lck}$ tyrosine kinase. Further, the compounds of the present invention are expected to be useful in the prevention or treatment of those diseases or medical conditions which are mediated alone or in part by inhibition of the enzyme $p56^{lck}$, i.e. the compounds may be used to produce a $p56^{lck}$ enzyme inhibitory effect in a warm-blooded animal in need of such treatment. Specifically, the compounds of the present invention are expected to be useful in the prevention or treatment of autoimmune conditions or diseases such as inflammatory diseases (for example rheumatoid arthritis, inflammatory bowel disease, glomerulonephritis and lung fibrosis), multiple sclerosis, psoriasis, hypersensitivity reactions of the skin, atherosclerosis, restenosis, allergic asthma and insulin-dependent diabetes. In particular the compounds of the present invention are expected to be useful in the prevention or treatment of the acute rejection of transplanted tissue or organs.

Thus according to this aspect of the invention there is provided the use of a quinoline derivative of the Formula I, or a pharmaceutically-acceptable salt thereof, as defined hereinbefore in the manufacture of a medicament for use in the prevention or treatment of T cell mediated diseases or medical conditions in a warm-blooded animal such as man.

According to a further feature of this aspect of the invention there is provided a method for the prevention or treatment of T cell mediated diseases or medical conditions in a warm-blooded animal, such as man, in need of such treatment which comprises administering to said animal an effective amount of a quinoline derivative of the Formula I, or a pharmaceutically-acceptable salt thereof, as defined hereinbefore.

According to a further feature of the invention there is provided the use of a quinoline derivative of the Formula I, or a pharmaceutically-acceptable salt thereof, as defined hereinbefore in the manufacture of a medicament for use in the prevention or treatment of those pathological conditions which are sensitive to inhibition of one or more of the multiple tyrosine-specific protein kinases which are involved in the early signal transduction steps which lead to T cell activation.

According to a further feature of the invention there is provided a method for the prevention or treatment of those pathological conditions which are sensitive to inhibition of one or more of the multiple tyrosine-specific protein kinases which are involved in the early signal transduction steps which lead to T cell activation which comprises administering to said animal an effective amount of a quinoline derivative of the Formula I, or a pharmaceutically-acceptable salt thereof, as defined hereinbefore.

As stated above the size of the dose required for the therapeutic or prophylactic treatment of T cell mediated disease will necessarily be varied depending on the host treated, the route of administration and the severity of the illness being treated. A unit dose in the range, for example, 0.5 mg/kg to 75 mg/kg body weight, preferably 0.5 mg/kg to 30 mg/kg body weight, is envisaged, given if required in divided doses.

We have also found that at higher doses the compounds of the present invention possess anti-proliferative properties which are believed to arise from their Class I (EGF type) receptor tyrosine kinase inhibitory activity. Accordingly the compounds of the present invention are expected to be useful in the treatment of diseases or medical conditions mediated alone or in part by Class I receptor tyrosine kinase enzymes, i.e. the compounds may be used to produce a Class I receptor tyrosine kinase inhibitory effect in a warm-blooded animal in need of such treatment. Thus the compounds of the present invention provide a method for treating the proliferation of malignant cells characterised by inhibition of Class I receptor tyrosine kinase enzymes, i.e.

the compounds may be used to produce an anti-proliferative effect mediated alone or in part by the inhibition of Class I receptor tyrosine kinase. Accordingly the compounds of the present invention are expected to be useful in the treatment of cancer by providing an anti-proliferative effect, particularly in the treatment of Class I receptor tyrosine kinase sensitive cancers such as cancers of the breast, lung, colon, rectum, stomach, prostate, bladder, pancreas and ovary. The compounds of the present invention are also expected to be useful in the treatment of other cell-proliferation diseases such as psoriasis, benign prostatic hypertrophy, atherosclerosis and restenosis.

According to this aspect of the invention there is provided the use of a quinoline derivative of the formula I, or a pharmaceutically-acceptable salt thereof, as defined hereinbefore in the manufacture of a medicament for use in the production of an anti-proliferative effect in a warm-blooded animal such as man.

According to a further feature of this aspect of the invention there is provided a method for producing an anti-proliferative effect in a warm-blooded animal, such as man, in need of such treatment which comprises administering to said animal an effective amount of a quinoline derivative of the formula I, or a pharmaceutically-acceptable salt thereof, as defined hereinbefore.

The size of the dose required to produce an anti-proliferative effect in a warm-blooded animal such as man will necessarily be varied depending on the host treated, the route of administration and the severity of the illness being treated. A unit dose in the range, for example, 5 mg/kg to 150 mg/kg body weight, preferably 5 mg/kg to 100 mg/kg body weight, is envisaged, given if required in divided doses.

The compounds of this invention may be used in combination with other drugs and therapies used in the treatment of T cell mediated disease. For example, the compounds of the Formula I could be used in combination with drugs and therapies used in the treatment of autoimmune conditions or diseases such as inflammatory diseases (for example rheumatoid arthritis, inflammatory bowel disease, glomerulonephritis and lung fibrosis), multiple sclerosis, psoriasis, hypersensitivity reactions of the skin, atherosclerosis, restenosis, allergic asthma and insulin-dependent diabetes. In particular the compounds of the Formula I could be used in combination with drugs and therapies such as cyclosporin A used in the prevention or treatment of the acute rejection of transplanted organs.

For example, the compounds of the Formula I are of value in the treatment of certain inflammatory and non-inflammatory diseases which are currently treated with a cyclooxygenase-inhibitory non-steroidal anti-inflammatory drug (NSAID) such as indomethacin, ketorolac, acetylsalicyclic acid, ibuprofen, sulindac, tolmetin and piroxicam. Co-administration of a compound of the Formula I with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises a compound of the Formula I, or a pharmaceutically-acceptable salt thereof, in conjunction or admixture with a cyclooxygenase inhibitory non-steroidal anti-inflammatory agent, and a pharmaceutically-acceptable diluent or carrier.

The compounds of the invention may also be used with anti-inflammatory agents such as an inhibitor of the enzyme 5-lipoxygenase. The compounds of the invention may also be used with anti-inflammatory agents such as an inhibitor of the enzyme COX-2 such as celecoxib or rofecoxib.

The compounds of the Formula I may also be used in the treatment of conditions such as rheumatoid arthritis in combination with antiarthritic agents such as gold, methotrexate, steroids and penicillinamine, and in conditions such as osteoarthritis in combination with steroids.

The compounds of the present invention may also be administered in degradative diseases, for example osteoarthritis, with chondroprotective, anti-degradative and/or reparative agents such as Diacerhein, hyaluronic acid formulations such as Hyalan, Rumalon, Arteparon and glucosamine salts such as Antril.

The compounds of the Formula I may be be used in the treatment of asthma in combination with antiasthmatic agents such as bronchodilators and leukotriene antagonists.

The anti-proliferative treatment defined hereinbefore may be applied as a sole therapy or may involve, in addition to the quinoline derivative of the invention, conventional radiotherapy or one or more other anti-tumour substances, for example cytotoxic or cytostatic anti-tumour substances, for example those selected from, for example, mitotic inhibitors, for example vinblastine, vindesine and vinorelbine; alkylating agents, for example cis-platin, carboplatin and cyclophosphamide; antimetabolites, for example 5-fluorouracil, tegafur, methotrexate, cytosine arabinoside and hydroxyurea, or, for example, one of the preferred antimetabolites disclosed in European Patent Application No. 239362 such as N-{5-[N-(3,4-dihydro-2-methyl-4-oxoquinazolin-6-ylmethyl)-N-methylamino]-2-thenoyl)}-L-glutamic acid; intercalating antibiotics, for example adriamycin, mitomycin and bleomycin; enzymes, for example asparaginase; topoisomerase inhibitors, for example etoposide and camptothecin; biological response modifiers, for example interferon; and anti-hormones, for example antioestrogens such as tamoxifen, for example antiandrogens such as 4'-cyano-3-(4-fluorophenylsulphonyl)-2-hydroxy-2-methyl-3'-(trifluoromethyl)propionanilide or, for example LHRH antagonists or LHRH agonists such as goserelin, leuprorelin or buserelin and hormone synthesis inhibitors, for example aromatase inhibitors such as those disclosed in European Patent Application No. 0296749, for example 2,2'-[5-(1H-1,2,4-triazol-1-ylmethyl)-1,3-phenylene]bis(2-methylpropionitrile), and, for example, inhibitors of 5α-reductase such as 17β-(N-tert-butylcarbamoyl)-4-aza-5α-androst-1-en-3-one. Such conjoint treatment may be achieved by way of the simultaneous, sequential or separate dosing of the individual components of the treatment. According to this aspect of the invention there is provided a pharmaceutical product comprising a quinoline derivative of the formula I as defined hereinbefore and an additional anti-tumour substance as defined hereinbefore for the conjoint treatment of cancer.

If formulated as a fixed dose such combination products employ the compounds of this invention within the dosage range described herein and the other pharmaceutically-active agent within its approved dosage range. Sequential use is contemplated when a combination formulation is inappropriate.

Although the compounds of the Formula I are primarily of value as therapeutic agents for use in warm-blooded animals (including man), they are also useful whenever it is required to inhibit the effects of T cell activation. Thus, they are useful as pharmacological standards for use in the development of new biological tests and in the search for new pharmacological agents.

The invention will now be illustrated in the following non-limiting Examples in which, unless otherwise stated:

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (HPLC) was performed on C18 reverse phase silica, for example on a Dynamax C-18 60 Å preparative reversed-phase column;

(iv) yields, where present, are given for illustration only and are not necessarily the maximum attainable;

(v) in general, the end-products of the Formula I have satisfactory microanalyses and their structures were confirmed by nuclear magnetic resonance (NMR) and/or mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Varian Gemini 2000 spectrometer operating at a field strength of 300 MHz or a Bruker AM250 spectrometer operating at a field strength of 250 MHz]; the following abbreviations have been used: s, singlet; d, doublet; q, quartet; t, triplet; m, multiplet; br, broad;

(vi) intermediates were not generally fully characterised and purity was assessed by thin layer chromatographic, HPLC, infra-red (IR) and/or NMR analysis;

(vii) melting points are uncorrected and were determined using a Mettler SP62 automatic melting point apparatus or an oil-bath apparatus; melting points for the end-products of the Formula I were determined after crystallisation from a conventional organic solvent such as ethanol, methanol, acetone, ether or hexane, alone or in admixture; and (viii) the following abbreviations have been used:
DMF N,N-dimethylformamide
DMSO dimethylsulphoxide
THF tetrahydrofuran

EXAMPLE 1

4-(4-chloro-2-fluorophenoxy)-7-methoxy-N-(3-morpholinopropyl)quinoline-6-carboxamide N-Hydroxybenzotriazole (0.104 g), triethylamine (0.095 ml), N-(3-aminopropyl)morpholine (0.11 ml) and 1-(3-dimethylaminopropyl)-3-ethylcarbodiimide hydrochloride (0.142 g) were added in turn to a stirred mixture of 4-(4-chloro-2-fluorophenoxy)-7-methoxyquinoline-6-carboxylic acid (0.2 g) in DMF (5 ml). The reaction mixture was stirred at ambient temperature for 16 hours. Water (20 ml) was added and the resultant suspension was transferred onto a C18 reversed-phase silica gel chromatography column and eluted with a decreasingly polar solvent gradient of water and acetonitrile. There was thus obtained the title compound (0.175 g); NMR Spectrum: (DMSOd$_6$) 1.72 (m, 2H), 2.38 (m, 6H), 3.35 (m, 2H), 3.56 (m, 4H), 4.01 (s, 3H), 6.56 (d, 1H), 7.42–7.59 (m, 3H), 7.76 (m, 1H), 8.38 (m, 1H), 8.51 (s, 1H), 8.68 (d, 1H); Mass Spectrum: M+H$^+$ 474 & 476.

The 4-(4-chloro-2-fluorophenoxy)-7-methoxyquinoline-6-carboxylic acid used as a starting material was prepared as follows:

A suspension of methyl 4-amino-2-methoxybenzoate (26.5 g) in isopropanol (500 ml) was stirred and heated to 50° C. for 10 minutes. 2,2-Dimethyl-5-methoxymethylene-1,3-dioxane-4,6-dione (methoxymethylene Meldrum's Acid, 25.6 g) was added and the resultant suspension was warmed to 80° C. and stirred for 40 minutes. The reaction mixture was allowed cool to ambient temperature and the white precipitate was isolated and washed with diethyl ether. There was thus obtained 2,2-dimethyl-5-(3-methoxy-4-methoxycarbonyl-anilinomethylene)-1,3-dioxane-4,6-dione (40.5 g); NMR Spectrum: (CDCl$_3$) 1.77 (s, 6H), 3.88 (s, 3H), 3.96 (s, 3H), 6.75 (s, 1H), 6.87 (d, 1H), 7.92 (d, 1H), 8.67 (d, 1H), 11.29 (d, 1H); Mass Spectrum: M+H$^+$ 279.

A suspension of a portion (25 g) of the material so obtained in a mixture of diphenyl ether (225 ml) and biphenyl (75 ml) was stirred and heated to 240° C. for 1 hour. The solution was allowed to cool to ambient temperature. The resultant precipitate was isolated and washed with diethyl ether. There was thus obtained methyl 7-methoxy-4-oxo-1,4-dihydroquinoline-6-carboxylate (14 g); NMR Spectrum: (DMSOd$_6$) 3.81 (s, 3H), 3.89 (s, 3H), 5.99 (d, 1H), 7.01 (s, 1H), 7.85 (m, 1H), 8.42 (s, 1H), 11.71 (broad s, 1H); Mass Spectrum: M+H$^+$ 234.

A mixture of a portion (3.9 g) of the material so obtained, thionyl chloride (50 ml) and DMF (a few drops) and stirred and heated to reflux for 2 hours. The resultant mixture was evaporated and the residue was azeotroped with toluene (2×100 ml). The residue was partitioned between methylene chloride and a dilute aqueous sodium bicarbonate solution. The organic phase was washed with a saturated aqueous sodium bicarbonate solution, dried over magnesium sulphate and evaporated. The residue was triturated under a 1:1 mixture of isohexane and diethyl ether and the resultant precipitate was isolated and washed with isohexane. There was thus obtained methyl 4-chloro-7-methoxyquinoline-6-carboxylate (3.7 g); NMR Spectrum: (CDCl$_3$) 3.99 (s, 3H), 4.04 (s, 3H), 7.38 (d, 1H), 7.52 (s, 1H), 8.62 (s, 1H), 8.75 (d, 1H); Mass Spectrum: M+H$^+$ 252 & 254.

A mixture of the material so obtained, 4-chloro-2-fluorophenol (4.05 g), potassium carbonate (7 g) and DMF (100 ml) was stirred and heated to 100° C. for 7 hours. A second portion (7 g) of potassium carbonate was added and the mixture heated to 100° C. for a further 16 hours. The mixture was allowed to cool to ambient temperature and was partitioned between ethyl acetate and water. The aqueous phase was re-extracted with ethyl acetate and the combined organic phases were washed with a saturated aqueous sodium chloride solution, dried over magnesium sulphate and evaporated. The residue was triturated under isohexane and the resultant precipitate was isolated and washed with isohexane. There was thus obtained methyl 4-(4-chloro-2-fluorophenoxy)-7-methoxyquinoline-6-carboxylate (3.8 g); NMR Spectrum: (CDCl$_3$) 3.98 (s, 3H), 4.05 (s, 3H), 6.39 (m, 1H), 7.19–7.35 (m, 3H), 7.51 (s, 1H), 8.67 (d, 1H), 8.81 (s, 1H); Mass Spectrum: M+H$^+$ 362 & 364.

A mixture of a portion (3.35 g) of the material so obtained, lithium hydroxide monohydrate (2.4 g), THF (70 ml), water (35 ml) and methanol (35 ml) was stirred at ambient temperature for 3 hours. The mixture was evaporated and the residue was partitioned between ethyl acetate and water. The aqueous phase was re-extracted with ethyl acetate. The aqueous phase was acidified to pH4 by the dropwise addition of 2N aqueous hydrochloric acid. The resultant precipitate was isolated and dried. Thus was obtained 4-(4-chloro-2-fluorophenoxy)-7-methoxyquinoline-6-carboxylic acid (2.1 g). NMR Spectrum: (DMSOd$_6$) 3.97 (s, 3H), 6.59 (d, 1H), 7.41–7.61 (m, 3H), 7.76 (m, 1H) 8.54 (s, 1H), 8.7 (d, 1H); Mass Spectrum: M+H$^+$ 348 & 350.

EXAMPLE 2

Using an analogous procedure to that described in Example 1, the appropriate 4-phenoxyquinoline-6-carboxylic acid was reacted with the appropriate amine to give the compounds described in Table I.

TABLE I

| No. | $(R^4)_n$ | $R^1$ | $R^2$ | Note |
|---|---|---|---|---|
| 1 | 4-chloro-2-fluoro | 2-(2-oxoimidazolidin-1-yl)ethyl | H | (a) |
| 2 | 4-chloro-2-fluoro | 2-(4-aminophenyl)ethyl | H | (b) |
| 3 | 4-chloro-2-fluoro | 3-phenylpropyl | H | (c) |
| 4 | 4-chloro-2-fluoro | 2-(2-pyridyl)ethyl | H | (d) |
| 5 | 4-chloro-2-fluoro | 2-morpholinoethyl | H | (e) |
| 6 | 4-chloro-2-fluoro | 2-(2,4-dioxo-5-methylthiazolidin-3-yl)ethyl | H | (f) |
| 7 | 4-chloro-2-fluoro | 2-(2,4-dioxoimidazolidin-1-yl)ethyl | H | (g) |
| 8 | 4-chloro-2-fluoro | 2-(2-oxopyrrolidin-1-yl)ethyl | H | (h) |
| 9 | 4-chloro-2-fluoro | 3-(2-oxopyrrolidin-1-yl)propyl | H | (i) |
| 10 | 4-chloro-2-fluoro | 3-(4-methylpiperazin-1-yl)propyl | H | (j) |
| 11 | 4-chloro-2-fluoro | 3-(2,6-dioxopiperidin-1-yl)propyl | H | (k) |
| 12 | 4-chloro-2-fluoro | 2-methoxyethyl | H | (l) |
| 13 | 4-chloro-2-fluoro | 3-methoxypropyl | H | (m) |
| 14 | 4-chloro-2-fluoro | 2-methylthioethyl | H | (n) |
| 15 | 4-chloro-2-fluoro | 3-methylthiopropyl | H | (o) |
| 16 | 4-chloro-2-fluoro | 2-methylsulphonylethyl | H | (p) |
| 17 | 4-chloro-2-fluoro | 2-(N-propylsulphamoyl)ethyl | H | (q) |
| 18 | 4-chloro-2-fluoro | 3-(1-imidazolyl)propyl | H | (r) |
| 19 | 4-chloro-2-fluoro | 4-(1-imidazolyl)butyl | H | (s) |
| 20 | 4-chloro-2-fluoro | 5-(1-imidazolyl)pentyl | H | (t) |
| 21 | 4-chloro-2-fluoro | 2-(1-imidazolyl)ethyl | H | (u) |
| 22 | 4-chloro-2-fluoro | 2-(4-imidazolyl)ethyl | H | (v) |
| 23 | 4-chloro-2-fluoro | 2-(2-thienyl)ethyl | H | (w) |

Notes (a) The product gave the following data: NMR Spectrum: ($CDCl_3$) 3.42–3.63 (m, 6H), 3.72 (m, 2H), 4.12 (s, 3H), 4.38 (s, 1H), 6.41 (d, 1H), 7.14–7.32 (m, 3H), 7.52 (s, 1H), 8.19 (m, 1H), 8.64 (d, 1H), 9.21 (s, 1H); Mass Spectrum: $M+H^+$ 459 & 461.

(b) The product gave the following data: NMR Spectrum: ($CDCl_3$) 2.86 (t, 2H), 3.77 (m, 2H), 3.94 (s, 3H), 6.39 (d, 1H), 6.71 (d, 2H), 7.08 (d, 2H), 7.19–7.33 (m, 3H), 7.5 (s, 1H), 7.91 (t, 1H), 8.66 (d, 1H), 9.23 (s, 1H); Mass Spectrum: $M+H^+$ 466 & 468.

(c) The product gave the following data: NMR Spectrum: ($CDCl_3$) 2.01 (m, 2H), 2.76 (t, 2H), 3.57 (m, 2H), 4.11 (s, 3H), 6.4 (m, 1H), 7.13–7.34 (m, 8H), 7.56 (s, 1H), 7.88 (t, 1H), 8.66 (d, 1H), 9.25 (s, 1H); Mass Spectrum: $M+H^+$ 465 & 467.

(d) The product gave the following data: NMR Spectrum ($CDCl_3$) 3.16 (t, 2H), 3.97 (q, 2H), 4.0 (s, 3H), 6.39 (d, 1H), 7.15–7.33 (m, 5H), 7.48 (s, 1H), 7.64 (m, 1H), 8.43 (m, 1H), 8.6 (m, 1H), 8.62 (d, 1H), 9.23 (s, 1H); Mass Spectrum: $M+H^+$ 452 & 454.

(e) The product gave the following data: NMR Spectrum: ($CDCl_3$) 2.55 (m, 6H), 3.64 (m, 2H), 3.78 (m, 4H), 4.12 (s, 3H), 6.39 (d, 1H), 7.11–7.32 (m, 3H), 7.51 (s, 1H), 8.39 (m, 1H), 8.64 (d, 1H), 9.26 (s, 1H); Mass Spectrum: $M+H^+$ 460 & 462.

(f) The product gave the following data: Mass Spectrum: $M+H^+$ 504 & 506.

(g) The product gave the following data: Mass Spectrum: $M+H^+$ 473 & 475.

(h) The product gave the following data: Mass Spectrum: $M+H^+$ 458 & 460. The 2-(2-oxopyrrolidin-1-yl) ethylamine, used as a starting material, was obtained as described in Chem. Express, 1993, 8, 825–828.

(i) The product gave the following data: Mass Spectrum: $M+H^+$ 472 & 474.

(j) The product gave the following data: Mass Spectrum: $M+H^+$ 487 & 489.

(k) The product gave the following data: Mass Spectrum: $M+H^+$ 500 & 502. The 3-(2,6,dioxopiperidin-1-yl) propylamine, used as a starting material, was obtained using an analogous procedure to that described in J. Amer. Chem. Soc., 1965, 87, 2003.

(l) The product gave the following data: Mass Spectrum: $M+H^+$ 405 & 407.

(m) The product gave the following data: Mass Spectrum: $M+H^+$ 419 & 421.

(n) The product gave the following data: Mass Spectrum: $M+H^+$ 421 & 423.

(o) The product gave the following data: Mass Spectrum: $M+H^+$ 435 & 437.

(p) The product gave the following data: Mass Spectrum: $M+H^+$ 453 & 455. The 2-methylsulphonylethylamine, used as a starting material, was obtained as described in Biochem. Pharmacol., 1989, 38, 399–406.

(q) The product gave the following data: Mass Spectrum: $M+H^+$ 496 & 498.

(r) The product gave the following data: Mass Spectrum: $M+H^+$ 455 & 457.

(s) The product gave the following data: Mass Spectrum: $M+H^+$ 469 & 471. The 4-(1-imidazolyl)butylamine, used as a starting material, was obtained as described in J. Med. Chem., 1986, 29, 523–530.

(t) The product gave the following data: Mass Spectrum: $M+H^+$ 483 & 485. The 5-(1-imidazolyl)pentylamine, used as a starting material, was obtained as described in J. Med. Chem., 1986, 29, 523–530.

(u) The product gave the following data: Mass Spectrum: $M+H^+$ 441 & 443. The 2-(1-imidazolyl)ethylamine, used as a starting material, was obtained as described in Synth. Commun., 1991, 21, 535.

(v) The product gave the following data: Mass Spectrum: $M+H^+$ 441 & 443.

(w) The product gave the following data: Mass Spectrum: $M+H^+$ 457 & 459.

EXAMPLE 3

N-[2-(4-chlorophenyl)ethyl]4-(4-chloro-2-fluorophenoxy)-7-methoxyquinoline-6-carboxamide Triethylamine (0.075 ml), N-hydroxybenzotriazole (0.075 g), 2-(4-chlorophenyl)ethylamine (0.092 g) and 1-(3-dimethylaminopropyl)-3-ethylcarbodiimide hydrochloride (0.137 g) were added in turn to a stirred mixture of 4-(4-chloro-2-fluorophenoxy)-7-methoxyquinoline-6-carboxylic acid (0.2 g) in acetonitrile (5 ml). The reaction mixture was stirred at ambient temperature for 16 hours. The mixture was evaporated and the residue was partitioned between chloroform and water. The organic phase was dried over magnesium sulphate and evaporated. The residue was triturated sequentially under diethyl ether and isohexane. The resultant precipitate was isolated. There was thus obtained the title compound (0.061 g); NMR Spectrum: ($CDCl_3$): 2.97 (t, 2H), 3.81 (m, 2H), 3.97 (s, 3H), 6.4 (d, 1H), 7.16–7.35 (m, 7H), 7.48 (s, 1H), 7.85 (m, 1H), 8.65 (d, 1H), 9.25 (s, 1H); Mass Spectrum: $M+H^+$ 486 & 488.

EXAMPLE 4

Using an analogous procedure to that described in Example 3, the appropriate 4-phenoxyquinoline-6-carboxylic acid was reacted with the appropriate amine to give the compound described in Table II.

TABLE II

| No. | $(R^4)_n$ | $R^1$ | $R^2$ | Note |
|---|---|---|---|---|
| 1 | 4-chloro-2-fluoro | 2-(4-methoxyphenyl)ethyl | H | (a) |

Note
(a) The product gave the following data: NMR Spectrum: (CDCl$_3$) 2.92 (t, 2H), 3.79 (m, 2H), 3.81 (s, 3H), 3.92 (s, 3H), 6.38 (d, 1H), 6.9 (d, 2H), 7.13–7.33 (m, 5H), 7.49 (s, 1H), 7.88 (t, 1H), 8.63 (d, 1H), 9.26 (s, 1H); Mass Spectrum: M+H$^+$ 481 & 483.

EXAMPLE 5

7-methoxy-N-(3-morpholinopropyl)-4-(4-phenoxyphenoxy)quinoline-6-carboxamide

A mixture of 4-chloro-7-methoxy-N-(3-morpholinopropyl)quinoline-6-carboxamide (0.154 g), 4-phenoxyphenol (0.11 g), potassium carbonate (0.207 g) and DMF (4 ml) was stirred and heated to 100° C. for 16 hours. The mixture was evaporated and the residue was partitioned between ethyl acetate and water. The aqueous phase was further extracted with ethyl acetate and the combined organic extracts were washed with a saturated aqueous sodium chloride solution, dried over magnesium sulphate and evaporated. The residue was purified by column chromatography on silica using increasingly polar mixtures of methylene chloride and methanol as eluent. There was thus obtained the title compound (0.13 g); NMR Spectrum: (CDCl$_3$) 1.86 (m, 2H), 2.47 (m, 6H), 3.6 (m, 2H), 3.7 (m, 4H), 4.11 (s, 3H), 6.48 (d, 1H), 7.04–7.18 (m, 7H), 7.37 (m, 2H), 7.51 (s, 1H), 8.02 (t, 1H), 8.65 (d, 1H), 9.19 (s, 1H); Mass Spectrum M+H$^+$ 514.

The 4-chloro-7-methoxy-N-(3-morpholinopropyl)quinoline-6-carboxamide used as a starting material was prepared as follows:

A mixture of methyl 4-chloro-7-methoxyquinoline-6-carboxylate (3 g) and concentrated aqueous hydrochloric acid (36%; 75 ml) was stirred and heated to 90° C. for 45 minutes. The mixture was allowed to cool to ambient temperature, poured into water (150 ml) and washed with methylene chloride. Evaporation of the aqueous phase gave 4-chloro-7-methoxyquinoline-6-carboxylic acid hydrochloride (2.8 g); NMR Spectrum: (DMSOd$_6$) 3.98 (s, 3H), 7.6 (s, 1H), 7.7 (d, 1H), 8.4 (s, 1H), 8.86 (d, 1H).

N-Hydroxybenzotriazole (0.235 g), triethylamine (1.8 ml), N-(3-aminopropyl)morpholine (2 ml) and 1-(3-dimethylaminopropyl)-3-ethylcarbodiimide hydrochloride (2.6 g) were added in turn to a mixture of the carboxylic acid so obtained and DMF (100 ml). The resultant reaction mixture was stirred at ambient temperature for 16 hours. The mixture was partitioned between methylene chloride and a 10:1 mixture of water and methanol. The organic phase was washed with a saturated aqueous sodium chloride solution, dried over magnesium sulphate and evaporated. The resultant oil was purified by column chromatography on silica using increasingly polar mixtures of methylene chloride and methanol as eluent. There was thus obtained the required starting material (1.9 g); NMR Spectrum:—(CDCl$_3$) 1.87 (m, 2H), 2.48 (m, 6H), 3.6 (m, 2H), 3.69 (m, 4H), 4.1 (s, 3H), 7.41 (d, 1H), 7.54 (s, 1H), 7.99 (m, 1H), 8.74 (d, 1H), 9.01 (s, 1H); Mass Spectrum: M+H$^+$ 363 & 365.

EXAMPLE 6

Using an analogous procedure to that described in Example 5, the appropriate 4-chloroquinoline-6-carboxamide was reacted with the appropriate phenol to give the compounds described in Table III.

TABLE III

| No. | $(R^4)_n$ | $R^1$ | Note |
|---|---|---|---|
| 1 | 3,4-dichloro | 3-morpholinopropyl | (a) |
| 2 | 3-dimethylamino | 3-morpholinopropyl | (b) |
| 3 | 4-acetamido | 3-morpholinopropyl | (c) |
| 4 | 4-methoxy | 3-morpholinopropyl | (d) |
| 5 | 4-phenyl | 3-morpholinopropyl | (e) |
| 6 | 4-methoxy | 2-(2-oxoimidazolidin-1-yl)ethyl | (f) |
| 7 | 4-bromo | 3-morpholinopropyl | (g) |
| 8 | 3-bromo | 3-morpholinopropyl | (h) |
| 9 | 4-nitro | 3-morpholinopropyl | (i) |
| 10 | 4-chloro | 3-morpholinopropyl | (j) |
| 11 | 4-benzoyl | 3-morpholinopropyl | (k) |
| 12 | 3-cyano | 3-morpholinopropyl | (l) |
| 13 | 4-cyano | 3-morpholinopropyl | (m) |
| 14 | 2-methoxy | 3-morpholinopropyl | (n) |
| 15 | 3-methoxy | 3-morpholinopropyl | (o) |
| 16 | 4-phenoxy | 2-(2-oxoimidazolidin-1-yl)ethyl | (p) |
| 17 | 3-dimethylamino | 2-(2-oxoimidazolidin-1-yl)ethyl | (q) |
| 18 | 3-methoxy | 2-(2-oxoimidazolidin-1-yl)ethyl | (r) |
| 19 | 2-methoxy | 2-(2-oxoimidazolidin-1-yl)ethyl | (s) |
| 20 | 3,4,5-trimethoxy | 2-(2-oxoimidazolidin-1-yl)ethyl | (t) |
| 21 | 3-cyano | 2-(2-oxoimidazolidin-1-yl)ethyl | (u) |
| 22 | 3-methoxy | 3-(2-oxopyrrolidin-1-yl)propyl | (v) |
| 23 | 2-fluoro-4-chloro | 2-dimethylaminoethyl | (w) |
| 24 | 3,4-dichloro | 2-dimethylaminoethyl | (x) |
| 25 | 4-phenoxy | 2-(2-pyridyl)ethyl | (y) |
| 26 | 4-methoxy | 2-(2-pyridyl)ethyl | (z) |
| 27 | 3-morpholino | 2-(2-pyridyl)ethyl | (aa) |
| 28 | 4-methylthio | 2-(2-pyridyl)ethyl | (bb) |
| 29 | 3-phenoxy | 2-(2-pyridyl)ethyl | (cc) |
| 30 | 3-phenoxy | 3-(1-imidazolyl)propyl | (dd) |
| 31 | 4-methylthio | 3-(1-imidazolyl)propyl | (ee) |
| 32 | 4-(3,5-diiodopyrid-4-yloxy) | 3-morpholinopropyl | (ff) |

Notes
The product gave the following data: NMR Spectrum: (CDCl$_3$) 1.95 (broad s, 2H), 2.61 (broad s, 6H), 3.61 (m, 2H), 3.78 (broad s, 4H), 4.13 (s, 3H), 6.51 (d, 2H), 7.06 (m, 1H), 7.32 (d, 1H), 7.54 (m, 2H), 8.1 (broad s, 1H), 8.69 (d, 1H), 9.13 (s, 1H); Mass Spectrum: M+H$^+$ 491, 493 & 495.

The product gave the following data: NMR Spectrum: (CDCl₃) 1.86 (m, 2H), 2.48 (m, 6H), 2.97 (s, 6H), 3.6 (m, 2H), 3.69 (m, 4H), 4.1 (s, 3H), 6.49 (m, 2H), 6.54 (d, 1H), 6.63 (m, 1H), 7.27 (m, 1H), 7.48 (s, 1H), 8.01 (t, 1H), 8.61 (d, 1H), 9.19 (s, 1H); Mass Spectrum: M+H⁺ 465.

The product gave the following data: NMR Spectrum: (CDCl₃) 1.81 (m, 2H), 2.11 (s, 3H), 2.42 (m, 6H), 3.55 (m, 2H), 3.64 (m, 4H), 4.04 (s, 3H), 6.34 (d, 1H), 6.95 (d, 2H), 7.44 (s, 1H), 7.65 (d, 2H), 8.11 (t, 1H), 8.45 (s, 1H), 8.53 (d, 1H), 9.08 (s, 1H); Mass Spectrum: M+H⁺ 479.

(d) The product gave the following data: NMR Spectrum: (CDCl₃) 1.86 (m, 2H), 2.49 (m, 6H), 3.6 (m, 2H), 3.7 (m, 4H), 3.85 (s, 3H), 4.1 (s, 3H), 6.41 (d, 1H), 6.98 (d, 2H), 7.1 (d, 2H), 7.5 (s, 1H), 8.02 (m, 1H), 8.61 (d, 1H), 9.19 (s, 1H); Mass Spectrum: M+H⁺ 452.

(e) The product gave the following data: NMR Spectrum: (CDCl₃) 1.87 (m, 2H), 2.49 (m, 6H), 3.61 (q, 2H), 3.71 (m, 4H), 4.12 (s, 3H), 6.56 (d, 1H), 7.34 (s, 1H), 7.72–7.34 (m, 9H), 8.06 (t, 1H), 8.66 (d, 1H), 9.22 (s, 1H); Mass Spectrum: M+H⁺ 498.

(f) The product gave the following data: NMR Spectrum: (CDCl₃) 3.41–3.63 (m, 6H), 3.7 (m, 2H), 3.86 (s, 3H), 4.12 (s, 3H), 4.33 (s, 1H), 6.41 (d, 1H), 6.98 (d, 2H), 7.11 (d, 2H), 7.49 (s, 1H), 8.2 (m, 1H), 8.6 (d, 1H), 9.24 (s, 1H); Mass Spectrum: M+H⁺ 437.

The 4-chloro-7-methoxy-N-[2-(2-oxoimidazolidin-1-yl)ethyl]quinoline-6-carboxamide used as a starting material was prepared by the reaction of 4-chloro-7-methoxyquinoline-6-carboxylic acid hydrochloride and 2-(2-oxoimidazolidin-1-yl)ethylamine using an analogous procedure to that described in the last paragraph of the portion of Example 5 which is concerned with the preparation of starting materials. The required material gave the following characterising data: NMR Spectrum: (CDCl₃) 3.42–3.64 (m, 6H), 3.71 (m, 2H), 4.12 (s, 3H), 4.45 (m, 1H) 7.4 (d, 1H), 7.53 (s, 1H), 8.19 (m, 1H), 8.74 (d, 1H), 9.08 (s, 1H); Mass Spectrum: M+H⁺ 349 & 351.

(g) The product gave the following data: NMR Spectrum: (CDCl₃) 1.85 (m, 2H), 2.47 (m, 6H), 3.6 (q, 2H), 3.69 (m, 4H), 4.11 (s, 3H), 6.46 (d, 1H), 7.06 (d, 2H), 7.52 (s, 1H), 7.57 (d, 2H), 8.02 (m, 1H), 8.65 (d, 1H), 9.16 (s, 1H); Mass Spectrum: M+H⁺ 500 & 502.

(h) The product gave the following data: NMR Spectrum: (CDCl₃) 1.86 (m, 2H), 2.51 (m, 6H), 3.61 (q, 2H), 3.7 (m, 4H), 4.11 (s, 3H), 6.5 (d, 1H), 7.12 (m, 1H), 7.3 (m, 2H), 7.43 (m, 1H), 7.52 (s, 1H), 7.99 (m, 1H), 8.65 (d, 1H), 9.16 (s, 1H); Mass Spectrum: M+H⁺ 500 & 502.

(i) The product gave the following data: NMR Spectrum: (CDCl₃) 1.88 (m, 2H), 2.41–2.60 (broad s, 6H), 3.58 (m, 2H), 3.72 (broad s, 4H), 4.14(s, 3H), 6.53 (d, 1H), 6.96 (m, 1H), 7.09 (d, 2H), 7.23 (d, 2H), 7.54 (s, 2H), 8.05 (broad s, 1H), 8.25 (d, 2H), 8.68 (d, 1H), 9.19 (s, 1H); Mass Spectrum: M+H⁺ 559.

(j) The product gave the following data: NMR Spectrum: (CDCl₃) 1.86 (m, 2H), 2.48 (broad s, 6H), 3.6 (m, 2H), 3.71 (t, 4H), 4.11 (s, 3H), 6.48 (d, 1H), 7.07 (d, 2H), 7.15 (d, 2H), 7.34 (d, 2H), 7.52 (s, 1H), 8.04 (broad s, 1H), 8.65 (d, 1H), 9.19 (s, 1H); Mass Spectrum: M+H⁺ 548 & 550.

(k) The product gave the following data: NMR Spectrum: (DMSOd₆) 1.77 (m, 2H), 2.42 (broad s, 6H), 3.38 (m, 2H), 3.61 (t, 4H), 4.09(s, 3H), 6.85 (d, 1H), 7.48 (d, 2H), 7.63 (d, 2H), 7.74 (m, 2H), 7.84 (d, 2H), 7.96 (d, 2H), 8.44 (m, 1H), 8.55 (s, 1H), 881 (d, 1H); Mass Spectrum: M+H⁺ 526.

(l) The product gave the following data: NMR Spectrum: (CDCl₃) 1.86 (m, 2H), 2.47 (broad m, 6H), 3.58 (m, 2H), 3.71 (t, 4H), 4.11 (s, 3H), 6.5 (d, 1H), 7.45 (m, 2H), 7.56 (s, 1H), 7.62 (m, 2H), 8.05 (broad s, 1H), 8.72 (d, 1H), 9.13 (s, 1H); Mass Spectrum: M+H⁺ 447.

(m) The product gave the following data: NMR Spectrum: (CDCl₃) 1.86 (m, 2H), 2.48 (m, 6H), 3.59 (m, 2H), 3.71 (t, 4H), 4.13 (s, 3H), 6.58 (d, 1H), 7.25 (d, 2H), 7.55 (s, 1H), 7.74 (d, 2H), 8.02 (broad s, 1H), 8.62 (d, 1H), 9.09 (s, 1H); Mass Spectrum: M+H⁺ 447.

(n) The product gave the following data: NMR Spectrum: (CDCl₃) 1.87 (m, 2H), 2.45 (broad m, 6H), 3.58 (m, 2H), 3.68 (t, 4H), 3.76 (s, 3H), 4.1 (s, 3H), 6.32 (d, 1H), 7.05 (m, 2H), 7.17 (m, 1H), 7.3 (m, 1H), 7.41 (s, 1H), 8.02 (broad s, 1H), 8.58 (d, 1H), 9.22 (s, 1H); Mass Spectrum: M+H⁺ 452.

(o) The product gave the following data: NMR Spectrum: (CDCl₃) 1.82 (m, 2H), 2.46 (broad m, 6H), 3.62 (m, 2H), 3.72 (t, 4H), 3.84 (s, 3H), 4.1 (s, 3H), 6.53 (d, 1H), 6.76 (m, 2H), 6.87 (m, 1H), 7.35 (t, 1H), 7.52 (s, 1H), 8.03 (broad s, 1H), 8.64 (d, 1H), 9.17 (s, 1H), Mass Spectrum: M+H⁺ 452.

(p) The product gave the following data: NMR Spectrum: (CDCl₃) 3.42–3.62 (m, 6H), 3.7 (m, 2H), 4.12 (s, 3H), 4.29 (s, 1H), 6.47 (d, 1H), 7.01–7.17 (m, 7H), 7.38 (t, 2H), 7.5 (s, 1H), 8.21 (m, 1H), 8.64 (d, 1H), 9.24 (s, 1H); Mass Spectrum: M+H⁺ 499.

(q) The product gave the following data: NMR Spectrum: (CDCl₃) 2.97 (s, 6H), 3.41–3.61 (m, 6H), 3.7 (q, 2H), 4.12 (s, 3H), 4.27 (s, 1H), 6.47–6.55 (m, 3H), 6.62 (m, 1H), 7.29 (m, 1H), 7.49 (s, 1H), 8.19 (m, 1H), 8.61 (d, 1H), 9.25 (s, 1H); Mass Spectrum: M+H⁺ 450.

(r) The product gave the following data: NMR Spectrum: (CDCl₃) 3.42–3.52 (m, 6H), 3.71 (m, 2H), 3.84 (s, 3H), 4.11 (s, 3H), 6.42–6.54 (m, 2H), 6.73 (m, 1H), 6.85 (d, 1H), 7.11 (t, 1H), 7.34 (t, 1H), 7.49 (s, 1H), 8.17 (broad s, 1H), 8.63 (d, 1H), 9.23 (s, 1H); Mass Spectrum: M+H⁺ 437.

(s) The product gave the following data: NMR Spectrum: (CDCl₃) 3.41–3.63 (m, 6H), 3.7 (m, 2H), 3.76 (s, 3H), 4.12 (s, 3H), 4.31 (s, 1H), 6.32 (d, 1H), 7.05 (m, 2H), 7.18 (d, 1H), 7.33 (m, 2H), 7.49 (s, 1H), 8.16 (broad s, 1H), 8.58 (d, 1H), 9.28 (s, 1H); Mass Spectrum: M+H⁺ 437.

(t) The product gave the following data: NMR Spectrum: (CDCl₃) 3.43–3.63 (m, 6H), 3.71 (q, 2H), 3.84 (s, 6H), 3.89 (s, 3H), 4.13 (s, 3H), 4.3 (s, 1H), 6.43 (s, 2H), 6.53 (d, 1H), 7.5 (s, 1H), 8.19 (m, 1H), 8.65 (d, 1H), 9.22 (s, 1H); Mass Spectrum: M+H⁺ 497.

(u) The product gave the following data: NMR Spectrum: (CDCl₃) 3.41–3.62 (m, 6H), 3.72 (m, 2H), 4.12 (s, 3H), 4.38 (s, 1H), 6.48 (d, 1H), 7.14 (m, 2H), 7.45 (m, 1H), 7.52 (s, 1H), 7.59 (d, 2H), 8.24 (broad s, 1H), 8.7 (d, 1H), 9.13 (s, 1H); Mass Spectrum: M+H⁺ 432.

(v) The product gave the following data: NMR Spectrum: (CDCl₃) 1.86 (m, 2H), 2.06 (m, 2H), 2.42 (t, 2H), 3.4–3.53 (m, 6H), 3.82 (s, 3H), 4.17 (s, 3H), 6.5 (d, 1H), 6.71–6.79 (m, 2H), 6.84 (m, 1H), 7.35 (t, 1H), 7.51 (s, 1H), 8.49 (m, 1H), 8.63 (d, 1H), 9.21 (s, 1H); Mass Spectrum: M+H⁺ 450.

The 4-chloro-7-methoxy-N-[3-(2-oxopyrrolidin-1-yl)propyl]quinoline-6-carboxamide, used as a starting material, was prepared by the reaction of 4-chloro-7-methoxyquinoline-6-carboxylic acid hydrochloride and 3-(2-oxopyrrolidin-1-yl)propylamine using an analogous procedure to that described in the last paragraph of the portion of Example 5 which is concerned with the preparation of starting materials. The required material gave the following characterising data: Mass Spectrum: M+H⁺ 362 & 364.

(w) The product gave the following data: NMR Spectrum: (CDCl₃) 2.35 (s, 6H), 2.6 (m, 2H), 3.62 (q, 2H), 4.09 (s, 3H), 6.39 (d, 1H), 7.2–7.32 (m, 3H), 7.5 (s, 1H), 8.37 (m, 1H), 8.65 (d, 1H), 9.22 (s, 1H); Mass Spectrum: M+H$^+$ 418 & 420.

The 4-chloro-7-methoxy-N-(2-dimethylaminoethyl) quinoline-6-carboxamide, used as starting material, was prepared by reaction of 4-chloro-7-methoxyquinoline-6-carboxylic acid hydrochloride and 2-dimethylaminoethylamine using an analogous procedure to that described in the last paragraph of the portion of Example 5 which is concerned with the preparation of starting materials. The required material gave the following characterising data: NMR Spectrum: (CDCl$_3$) 2.35 (s, 6H), 2.6 (t, 2H), 3.63 (q, 2H), 4.1 (s, 3H), 7.39 (d, 1H), 7.53 (s, 1H), 8.32 (m, 1H), 8.73 (d, 1H), 9.06 (s, 1H); Mass Spectrum: M+H$^+$ 308 & 310.

(x) The product gave the following data: NMR Spectrum: (CDCl$_3$) 2.38 (s, 6H), 2.65 (t, 2H), 3.65 (q, 2H), 4.11 (s, 3H), 6.51 (d, 1H), 7.06 (m, 1H), 7.32 (d, 1H), 7.53 (s, 1H), 7.55 (s, 1H), 8.39 (m, 1H), 8.68 (d, 1H), 9.15 (s, 1H); Mass Spectrum: M+H$^+$ 434 & 436.

(y) The product gave the following data: NMR Spectrum: (CDCl$_3$) 3.17 (t, 2H), 3.97 (q, 2H), 4.0 (s, 3H), 6.47 (d, 1H), 7.04–7.21 (m, 9H), 7.38 (m, 2H), 7.45 (s, 1H), 7.65 (m, 1H), 8.45 (m, 1H), 8.68 (m, 2H), 9.26 (s, 1H); Mass Spectrum: M+H$^+$ 492.

The 4-chloro-7-methoxy-N-[2-(2-pyridyl)ethyl] quinoline-6-carboxamide, used as starting material, was prepared by reaction of 4-chloro-7-methoxyquinoline-6-carboxylic acid hydrochloride and 2-(2-pyridyl)ethylamine using an analogous procedure to that described in the last paragraph of the portion of Example 5 which is concerned with the preparation of starting materials.

(z) The product gave the following data: NMR Spectrum: (CDCl$_3$) 3.17 (t, 2H), 3.86 (s, 3H), 3.98 (q, 2H), 4.0 (s, 3H), 6.41 (d, 1H), 6.97 (d, 2H), 7.1 (d, 2H), 7.15–7.29 (m, 2H), 7.45 (s, 1H), 7.65 (td, 1H), 8.43 (m, 1H), 8.01 (d, 1H), 9.25 (s, 1H); Mass Spectrum: M+H$^+$ 430.

(aa) The product gave the following data: NMR Spectrum: (CDCl$_3$) 3.19 (m, 6H), 3.86 (m, 4H), 3.98 (q, 2H), 4.01 (s, 3H), 6.51 (d, 1H), 6.68 (d, 2H), 6.83 (m, 1H), 7.16–7.28 (m, 2H), 7.34 (t, 1H), 7.47 (s, 1H), 7.65 (m, 1H), 8.44 (m, 1H), 8.62 (d, 2H), 9.25 (s, 1H); Mass Spectrum: M+H$^+$ 485.

(bb) The product gave the following data: NMR Spectrum: (CDCl$_3$) 2.53 (s, 3H), 3.16 (t, 2H), 3.97 (q, 2H), 4.0 (s, 3H), 6.45 (d, 1H), 7.11 (d, 2H), 7.19 (m, 2H), 7.35 (s, 2H), 7.46 (s, 1H), 7.65 (m, 1H), 8.44 (m, 1H), 8.63 (m, 2H), 9.24 (s, 1H); Mass Spectrum: M+H$^+$ 446.

(cc) The product gave the following data: NMR Spectrum: (CDCl$_3$) 3.16 (t, 2H), 3.97 (q, 2H), 4.0 (s, 3H), 6.53 (d, 1H), 6.81 (t, 1H), 6.91 (m, 2H), 7.06–7.23 (m, 6H), 7.36 (m, 2H), 7.45 (s, 1H), 7.65 (m, 1H), 8.43 (m, 1H), 8.63 (m, 2H), 9.2 (s, 1H); Mass Spectrum: M+H$^+$ 492.

(dd) The product gave the following data: NMR Spectrum: (CDCl$_3$) 2.17 (m, 2H), 3.53 (q, 2H), 4.09 (t, 2H), 4.12 (s, 2H), 6.55 (d, 1H), 6.81 (t, 1H), 6.92 (m, 2H), 7.0 (s, 1H), 7.07 (m, 3H), 7.15 (t, 1H), 7.38 (m, 3H), 7.52 (d, 2H), 7.96 (m, 1H), 8.66 (d, 1H), 9.23 (s, 1H); Mass Spectrum: M+H$^+$ 495.

The 4-chloro-7-methoxy-N-[3-(1-imidazolyl)propyl] quinoline-6-carboxamide, used as starting material, was prepared by reaction of 4-chloro-7-methoxyquinoline-6-carboxylic acid hydrochloride and 3-(1-imidazolyl) propylamine using an analogous procedure to that described in the last paragraph of the portion of Example 5 which is concerned with the preparation of starting materials.

(ee) The product gave the following data: NMR Spectrum: (CDCl$_3$) 2.18 (m, 2H), 2.53 (s, 3H), 3.54 (q, 2H), 4.1 (t, 2H), 4.13 (s, 2H), 6.47 (d, 1H), 7.0 (s, 1H), 7.09 (s, 1H), 7.11 (d, 2H), 7.35 (d, 2H), 7.53 (s, 1H), 7.55 (s, 1H), 7.98 (m, 1H), 8.64 (d, 1H), 9.26 (s, 1H); Mass Spectrum: M+H$^+$ 449.

(ff) The product gave the following data: NMR Spectrum: (CDCl$_3$) 1.86 (m, 2H), 2.48 (m, 6H), 3.6 (m, 2H), 3.71 (t, 4H), 4.11 (s, 3H), 6.47 (d, 1H), 6.9 (d, 2H), 7.15 (d, 2H), 7.51 (s, 1H), 8.02 (broad s, 1H), 8.65 (d, 1H), 8.88 (s, 2H), 9.17 (s, 1H).

The 4-hydroxyphenyl 2,6-diiodo-4-pyridyl ether, used as starting material, was prepared as follows:

A mixture of 3,5-diiodo-4-pyridone (Liebig's Annalen, 1932, 494, 284; 20 g), phosphorus pentachloride (12 g) and phosphoryl chloride (50 ml) was stirred and heated to 130° C. for 6.5 hours. The mixture was cooled to ambient temperature and added cautiously to a mixture of ice and water. The resultant precipitate was isolated, washed with water and dried. There was thus obtained 4-chloro-3,5-diiodopyridine (17 g), m.p. 172–174° C.

Sodium hydride (50% suspension in mineral oil, 1.83 g) was washed with petroleum ether (b.p. 40–60° C.) and DMF (25 ml) was added to the residue. 4-Methoxyphenol (0.62 g) was added portionwise to the stirred suspension and the resultant mixture was stirred at ambient temperature for 15 minutes. 4-Chloro-3,5-diiodopyridine (1.83 g) was added and the mixture was stirred and heated to 110° C. for 5 minutes. The mixture was cooled to ambient temperature and water (200 ml) was added. The resultant precipitate was isolated, dried and recrystallised from petroleum ether (b.p. 80–100° C.). There was thus obtained the 3,5-diiodo-4-pyridyl 4-methoxyphenyl ether (1.87 g), m.p. 133–135° C.

After suitable repetition of the previous reaction, a solution of boron tribromide (5 g) in methylene chloride (19 ml) was added to a stirred solution of 3,5-diiodo-4-pyridyl 4-methoxyphenyl ether (4.53 g) in methylene chloride (135 ml). The resultant mixture was stirred at ambient temperature for 16 hours. The mixture was quenched with water and extracted with diethyl ether. The combined organic extracts were washed with water and a saturated aqueous sodium chloride solution, dried over sodium sulphate and evaporated. The residue was recrystallised from aqueous methanol. There was thus obtained 4-hydroxyphenyl 2,6-diiodo-4-pyridyl ether (2.3 g), m.p. 255–258° C.

EXAMPLE 7

4-(4-anilinophenoxy)-7-methoxy-N-(3-morpholinopropyl)quinoline-6-carboxamide

Aniline (0.03 ml) was added to a stirred mixture of 4-(4-bromophenoxy)-7-methoxy-N-(3-morpholinopropyl) quinoline-6-carboxamide (0.132 g), caesium carbonate (0.23 g), palladium acetate (0.01 g), 2,2'-bis (diphenylphosphino)-1,1'-binaphthyl (0.055 g) and toluene (5 ml) and the reaction mixture was stirred and heated to stirred and heated to 100° C. for 16 hours. The mixture was evaporated and the resultant residue was partitioned between ethyl acetate and water. The organic phase was washed with a saturated aqueous sodium chloride solution and dried over magnesium sulphate. The residue was purified by column chromatography on silica using increasingly polar mixtures of methylene chloride and methanol as eluent. There was thus obtained the title compound (0.103 g); NMR Spectrum: (CDCl$_3$) 1.86 (m, 2H), 2.49 (m, 6H), 3.6 (q, 2H), 3.7 (m, 4H), 4.1 (s, 3H), 5.77 (s, 1H), 6.5 (d, 1H), 6.96 (t, 1H), 7.04–7.17 (m, 6H), 7.3 (m, 2H), 7.5 (s, 1H), 8.02 (m, 1H), 8.63 (d, 1H), 9.19 (s, 1H); Mass Spectrum: M+H$^+$ 513.

EXAMPLE 8

Using an analogous procedure to that described in Example 7, the appropriate bromophenoxyquinoline-6- carboxamide was reacted with the appropriate amine or aniline to give the compounds described in Table IV.

TABLE IV

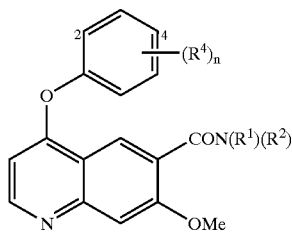

| No. | $(R^4)_n$ | $R^1$ | $R^2$ | Note |
|---|---|---|---|---|
| 1 | 4-(2-fluoro-4-chloroanilino) | 3-morpholinopropyl | H | (a) |
| 2 | 4-(N-methylanilino) | 3-morpholinopropyl | H | (b) |
| 3 | 3-(n-butylamino) | 3-morpholinopropyl | H | (c) |
| 4 | 3-(2-dimethylaminoethylamino) | 3-morpholinopropyl | H | (d) |

Notes (a) The product gave the following data: NMR Spectrum: (CDCl$_3$) 1.86 (m, 2H), 2.49 (m, 6H), 3.6 (q, 2H), 2.7 (m, 4H), 4.11 (s, 3H), 5.82 (m, 1H), 6.48 (d, 1H), 7.03–7.24 (m, 7H), 7.51 (s, 1H), 8.03 (m, 1H), 8.64 (m, 1H), 9.19 (s, 1H); Mass Spectrum: M+H$^+$ 565.

(b) The product gave the following data: NMR Spectrum: (CDCl$_3$) 1.87 (m, 2H), 2.49 (m, 6H), 3.34 (s, 3H), 3.6 (q, 2H), 3.71 (m, 4H), 4.09 (s, 3H), 6.52 (d, 1H), 6.62 (m, 1H), 6.69 (m, 1H), 6.8 (m, 1H), 7.08 (t, 1H), 7.15 (d, 2H), 7.21–7.38 (m, 3H), 7.48 (s, 1H), 8.01 (m, 1H), 8.62 (d, 1H), 9.14 (s, 1H); Mass Spectrum: M+H$^+$ 527.

(c) The product gave the following data: NMR Spectrum: (CDCl$_3$) 0.96 (t, 3H), 1.43 (s, 2H), 1.63 (m, 2H), 1.85 (m, 2H), 2.54 (m, 6H), 2.09 (t, 2H), 3.59 (q, 2H), 3.69 (m, 4H), 4.1 (s, 3H), 6.38 (m, 1H), 6.48 (m, 2H), 6.55 (d, 1H), 7.21 (m, 2H), 7.5 (s, 1H), 8.0 (m, 1H), 8.61 (d, 1H), 9.17 (s, 1H); Mass Spectrum: M+H$^+$ 493.

(d) The product gave the following data: NMR Spectrum: (CDCl$_3$) 1.85 (m, 2H), 2.25 (s, 6H), 2.49 (m, 6H), 2.55 (t, 2H), 3.11 (m, 2H), 3.6 (q, 2H), 3.69 (m, 4H), 4.1 (s, 3H), 4.49 (broad s, 1H), 6.4 (m, 1H), 6.46 (d, 1H), 6.53 (m, 2H), 7.21 (t, 1H), 7.49 (s, 1H), 8.0 (m, 1H), 8.62 (d, 1H), 9.16 (s, 1H); Mass Spectrum: M+H$^+$ 508.

EXAMPLE 9

Pharmaceutical Compositions

The following illustrate representative pharmaceutical dosage forms of the invention as defined herein (the active ingredient being termed "Compound X"), for therapeutic or prophylactic use in humans:

| (a) | Tablet I | mg/tablet |
|---|---|---|
| | Compound X | 100 |
| | Lactose Ph.Eur | 182.75 |
| | Croscarmellose sodium | 12.0 |
| | Maize starch paste (5% w/v paste) | 2.25 |
| | Magnesium stearate | 3.0 |

| (b) | Tablet II | mg/tablet |
|---|---|---|
| | Compound X | 50 |
| | Lactose Ph.Eur | 223.75 |
| | Croscarmellose sodium | 6.0 |
| | Maize starch | 15.0 |
| | Polyvinylpyrrolidone (5% w/v paste) | 2.25 |
| | Magnesium stearate | 3.0 |

| (c) | Tablet III | mg/tablet |
|---|---|---|
| | Compound X | 1.0 |
| | Lactose Ph.Eur | 93.25 |
| | Croscarmellose sodium | 4.0 |
| | Maize starch paste (5% w/v paste) | 0.75 |
| | Magnesium stearate | 1.0 |

| (d) | Capsule | mg/capsule |
|---|---|---|
| | Compound X | 10 |
| | Lactose Ph.Eur | 488.5 |
| | Magnesium | 1.5 |

| (e) | Injection I | (50 mg/ml) |
|---|---|---|
| | Compound X | 5.0% w/v |
| | 1 M Sodium hydroxide solution | 15.0% v/v |
| | 0.1 M Hydrochloric acid (to adjust pH to 7.6) | |
| | Polyethylene glycol 400 | 4.5% w/v |
| | Water for injection to 100% | |

| (f) | Injection II | (10 mg/ml) |
|---|---|---|
| | Compound X | 1.0% w/v |
| | Sodium phosphate BP | 3.6% w/v |
| | 0.1 M Sodium hydroxide solution | 15.0% v/v |
| | Water for injection to 100% | |

| (g) | Injection III | (1 mg/ml, buffered to pH6) |
|---|---|---|
| | Compound X | 0.1% w/v |
| | Sodium phosphate BP | 2.26% w/v |
| | Citric acid | 0.38% w/v |
| | Polyethylene glycol 400 | 3.5% w/v |
| | Water for injection to 100% | |

| (h) | Aerosol I | mg/ml |
|---|---|---|
| | Compound X | 10.0 |
| | Sorbitan trioleate | 13.5 |
| | Trichlorofluoromethane | 910.0 |
| | Dichlorodifluoromethane | 490.0 |

| (i) | Aerosol II | mg/ml |
|---|---|---|
| | Compound X | 0.2 |
| | Sorbitan trioleate | 0.27 |
| | Trichlorofluoromethane | 70.0 |
| | Dichlorodifluoromethane | 280.0 |
| | Dichlorotetrafluoroethane | 1094.0 |

| (j) | Aerosol III | mg/ml |
|---|---|---|
| | Compound X | 2.5 |
| | Sorbitan trioleate | 3.38 |
| | Trichlorofluoromethane | 67.5 |
| | Dichlorodifluoromethane | 1086.0 |
| | Dichlorotetrafluoroethane | 191.6 |

| (k) | Aerosol IV | mg/ml |
|---|---|---|
| | Compound X | 2.5 |
| | Soya lecithin | 2.7 |
| | Trichlorofluoromethane | 67.5 |
| | Dichlorodifluoromethane | 1086.0 |
| | Dichlorotetrafluoroethane | 191.6 |

| (l) | Ointment | ml |
|---|---|---|
| | Compound X | 40 mg |
| | Ethanol | 300 μl |
| | Water | 300 μl |

| | |
|---|---|
| 1-Dodecylazacycloheptan-2-one | 50 μl |
| Propylene glycol | to 1 ml |

Note

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

What is claimed is:

1. A quinoline compound of the Formula I

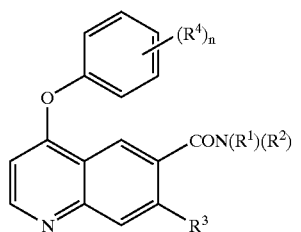

wherein n is 0, 1, 2 or 3 and each $R^4$, which may be the same or different, is halogeno, hydroxy, amino, nitro, trifluoromethyl, trifluoromethoxy, cyano, (1–6C)alkyl, (2–6C)alkenyl, (2–6C)alkynyl, (1–6C)alkoxy, (1–6C)alkylamino, di-[(1–6C)alkyl]amino, (2–6C)alkanoylamino, (1–6C)alkylthio, (1–6C)alkylsulphinyl, (1–6C)alkylsulphonyl, pyrrolidin-1-yl, piperidino, morpholino, piperazin-1-yl or 4-(1–6C)alkylpiperazin-1-yl, and any $CH_2$ or $CH_3$ group in a $R^4$ group optionally bears on each such $CH_2$ or $CH_3$ group a substituent selected from halogeno, hydroxy, amino, cyano, (1–6C)alkyl, (1–6C)alkoxy, (1–6C)alkylamino, di-[(1–6C)alkyl]amino and (2–6C)alkanoylamino, or $R^4$ is phenyl, phenoxy, anilino, N-(1–6C)alkylanilino, benzoyl, phenylthio, phenylsulphinyl, phenylsulphonyl, benzyl, pyridyl or pyridyloxy and the phenyl or pyridyl group in any of the 11 last-named substituents is optionally substituted with 1, 2 or 3 substituents, which may be the same or different, selected from halogeno, hydroxy, amino, nitro, trifluoromethyl, trifluoromethoxy, cyano, (1–6C)alkyl, (2–6C)alkenyl, (2–6C)alkynyl, (1–6C)alkoxy, (1–6C)alkylamino, di-[(1–6C)alkyl]amino and (2–6C)alkanoylamino, or $(R^4)_n$ is a (1–3C)alkylenedioxy substituent;

$R^1$ is hydrogen, (1–6C)alkyl, (2–6C)alkenyl or (2–6C)alkynyl;

$R^2$ is hydrogen, (1–6C)alkyl, (2–6C)alkenyl or (2–6C)alkynyl;

and wherein any $CH_2$ or $CH_3$ group in an $R^1$ or $R^2$ group optionally bears on each such $CH_2$ or $CH_3$ group a substituent selected from halogeno, hydroxy, amino, cyano, carbamoyl, sulphamoyl, (1–6C)alkoxy, (1–6C)alkylamino, di-[(1–6C)alkyl]amino, (2–6C)alkanoylamino, (1–6C)alkylthio, (1–6C)alkylsulphinyl, (1–6C)alkylsulphonyl, N-(1–6C)alkylcarbamoyl, N,N-di-[(1–6C)alkyl]carbamoyl, N-(1–6C)alkylsulphamoyl and N,N-di-[(1–6C)alkyl]sulphamoyl, or a substituent selected from aryl, aryloxy, arylamino, N-(1–6C)alkyl-arylamino, aryl-(1–6C)alkoxy, aryl-(1–6C)alkylamino, N-(1–6C)alkyl-aryl-(1–6C)alkylamino, aroylamino, N-arylcarbamoyl, aryl-(2–6C)alkanoylamino and N-[aryl-(1–6C)alkyl]carbamoyl, or a substituent selected from (3–7C)cycloalkyl, (3–7C)cycloalkyloxy, (3–7C)cycloalkylamino, N-(1–6C)alkyl-(3–7C)cycloalkylamino, (3–7C)cycloalkyl-(1–6C)alkoxy, (3–7C)cycloalkyl-(1–6C)alkylamino, N-(1–6C)alkyl-(3–7C)cycloalkyl-(1–6C)alkylamino, (3–7C)cycloalkylcarbonylamino, N-[(3–7C)cycloalkyl]carbamoyl, (3–7C)cycloalkyl-(2–6C)alkanoylamino and N-[(3–7C)cycloalkyl-(1–6C)alkyl]carbamoyl, or a substituent selected from heteroaryl, heteroaryloxy, heteroarylamino, N-(1–6C)alkyl-heteroarylamino, heteroaryl-(1–6C)alkoxy, heteroaryl-(1–6C)alkylamino, N-(1–6C)alkyl-heteroaryl-(1–6C)alkylamino, heteroarylcarbonylamino, N-heteroarylcarbamoyl, heteroaryl-(2–6C)alkanoylamino and N-[heteroaryl-(1–6C)alkyl]carbamoyl, or a substituent selected from heterocyclyl, heterocyclyloxy, heterocyclylamino, N-(1–6C)alkyl-heterocyclylamino, heterocyclyl-(1–6C)alkoxy, heterocyclyl-(1–6C)alkylamino, N-(1–6C)alkyl-heterocyclyl-(1–6C)alkylamino, heterocyclylcarbonylamino, N-heterocyclylcarbamoyl, heterocyclyl-(2–6C)alkanoylamino and N-[heterocyclyl-(1–6C)alkyl]carbamoyl, and wherein any aryl, (3–7C)cycloalkyl, heteroaryl or heterocyclyl group in a substituent on $R^1$ or $R^2$ optionally bears 1, 2 or 3 substituents, which may be the same or different, selected from halogeno, hydroxy, amino, nitro, trifluoromethyl, trifluoromethoxy, cyano, (1–6C)alkyl, (2–6C)alkenyl, (2–6C)alkynyl, (1–6C)alkoxy, (1–6C)alkylamino, di-[(1–6C)alkyl]amino and (2–6C)alkanoylamino and any (3–7C)cycloalkyl or heterocyclyl group on a $R^1$ or $R^2$ group optionally bears 1 or 2 oxo substituents; and $R^3$ is hydrogen, halogeno, hydroxy, amino, (1–6C)alkyl, (1–6C)alkoxy, (1–6C)alkylamino, di-[(1–6C)alkyl]amino or (2–6C)alkanoylamino;

or a pharmaceutically-acceptable salt thereof.

2. A quinoline compound of the Formula I according to claim 1 wherein n is 1, 2 or 3 and each $R^4$ group is independently selected from fluoro, chloro, bromo, hydroxy, amino, trifluoromethyl, methyl, methoxy, methylamino, dimethylamino, acetamido, phenyl and phenoxy and wherein said 2 last-named substituents optionally bear 1, 2 or 3 substituents selected from fluoro, chloro, bromo, methyl and methoxy;

$R^2$ is hydrogen;

$R^1$ is ethyl, propyl or butyl which bears 1 or 2 substituents selected from hydroxy, amino, cyano, methoxy, ethoxy, methylamino, ethylamino, dimethylamino, diethylamino, acetamido, phenyl, imidazolyl, pyridyl, pyrrolidinyl, imidazolidinyl, morpholinyl, piperidinyl and piperazinyl and wherein any of the 8 last-named substituents on $R^1$ optionally bears 1 or 2 further substituents selected from fluoro, chloro, bromo, hydroxy, amino, trifluoromethyl, cyano, methyl, methoxy, methylamino, dimethylamino and acetamido and wherein any of the pyrrolidinyl, imidazolidinyl, morpholinyl, piperidinyl and piperazinyl substituents on $R^1$ optionally bears 1 or 2 oxo substituents; and $R^3$ is methoxy;

or a pharmaceutically-acceptable salt thereof.

3. A quinoline compound of the Formula I according to claim 1 wherein n is 1, 2 or 3 and each $R^4$ group is independently selected from fluoro, chloro, bromo, hydroxy, amino, trifluoromethyl, cyano, methyl, ethyl, methoxy, ethoxy, methylamino, ethylamino, propylamino, butylamino, dimethylamino, diethylamino, acetamido, methylthio, piperidin-1-yl, piperidino, morpholino, piperazin-1-yl, 4-methylpiperazin-1-yl, phenyl, phenoxy, anilino, N-methylanilino, benzoyl, phenylthio, benzyl, 4-pyridyl and 4-pyridyloxy;

$R^2$ is hydrogen;

$R^1$ is ethyl, propyl or butyl which bears a substituent selected from hydroxy, amino, methoxy, methylamino, dimethylamino, acetamido, methylthio, methylsulphinyl, methylsulphonyl, N-methylcarbamoyl, N,N-dimethylcarbamoyl, N-methylsulphamoyl, N-ethylsulphamoyl, N-propylsulphamoyl, N,N-dimethylsulphamoyl, 4-chlorophenyl, 4-aminophenyl, 4-methoxyphenyl, 1-imidazolyl, 2-imidazolyl, 2-pyridyl, pyrrolidin-1-yl, 2-oxopyrrolidin-1-yl, 2-oxoimidazolidin-1-yl, 2,4-dioxoimidazolidin-1-yl, 5-methyl-2,4-dioxothiazolidin-3-piperidino, 2,6-dioxopiperidin-1-yl, morpholino, piperazin-1-yl and 4-methylpiperazin-1-yl;

and $R^3$ is methoxy;

or a pharmaceutically-acceptable salt thereof.

4. A quinoline compound of the Formula I according to claim 1 wherein n is 1 or 2 and each $R^4$ group is independently selected from fluoro, chloro, dimethylamino, acetamido, phenyl and phenoxy;

$R^2$ is hydrogen;

$R^1$ is ethyl or propyl which bears a substituent selected from 4-chlorophenyl, 4-aminophenyl, 4-methoxyphenyl, 2-pyridyl, 2-oxoimidazolidin-1-yl and morpholino; and $R^3$ is methoxy;

or a pharmaceutically-acceptable salt thereof.

5. A quinoline compound of the Formula I according to claim 1 selected from:

4-(4-chloro-2-fluorophenoxy)-7-methoxy-N-(3-morpholinopropyl)quinoline-6-carboxamide, 4-(3,4-dichlorophenoxy)-7-methoxy-N-(3-morpholinopropyl)quinoline-6-carboxamide, 4-(4-chloro-2-fluorophenoxy)-N-[2-(2-oxoimidazolidin-1-yl)ethyl]-7-methoxyquinoline-6-carboxamide and 7-methoxy-N-(3-morpholinopropyl)-4-(4-phenoxyphenoxy)quinoline-6-carboxamide;

or a pharmaceutically-acceptable salt thereof.

6. A process for the preparation of a quinoline compound of the Formula I, or a pharmaceutically-acceptable salt thereof, according to claim 1 which comprises (a) the reaction of a quinoline of the Formula II

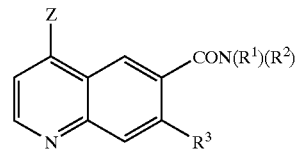

wherein Z is a displaceable group and $R^1$, $R^2$, $R^3$ and m have any of the meanings defined in claim 1 except that any functional group is protected if necessary, with a phenol of the Formula III

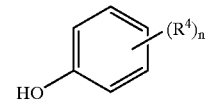

wherein $R^4$ and n have any of the meanings defined in claim 1 except that any functional group is protected if necessary, whereafter any protecting group that is present is removed by conventional means;

(b) the reaction of a carboxylic acid of the Formula VII, or a reactive compound thereof,

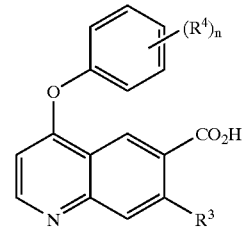

wherein $R^3$, $R^4$ and n have any of the meanings defined in claim 1 except that any functional group is protected if necessary, with an amine of the Formula V

wherein $R^1$ and $R^2$ have any of the meanings defined in claim 1 except that any functional group is protected if necessary, whereafter any protecting group that is present is removed by conventional means;

(c) for the preparation of those compounds of the Formula I wherein $R^4$ is an amino, (1–6C)alkylamino, di-[(1–6C)alkyl]amino, anilino or N-(1–6C)alkylanilino group, the reaction of a compound of the Formula VIII wherein $R^1$, $R^2$ and $R^3$ have any of the meanings defined in claim 1 except that any functional group is protected if necessary and Z is a displaceable group,

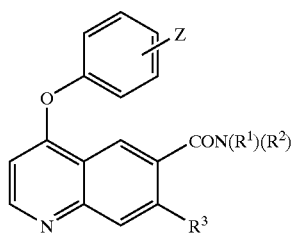

VIII with an amine or aniline as appropriate whereafter any protecting group that is present is removed by conventional means;

and when a pharmaceutically-acceptable salt of a quinoline compound of the Formula I is required it may be obtained by reaction of said quinoline compound with a suitable acid using a conventional procedure.

7. A pharmaceutical composition which comprises a quinoline compound of the Formula I, or a pharmaceutically-acceptable salt thereof, as defined in claim 1 in association with a pharmaceutically-acceptable diluent or carrier.

8. A method for the prevention or treatment of an autoimmune disease or medical condition in a warm-blooded animal in need thereof which comprises administering to said animal an effective amount of a quinoline compound of the Formula I, or a pharmaceutically-acceptable salt thereof, as defined in claim 1.

9. A method for producing an anti-inflammatory effect in a warm blooded animal in need thereof which comprises administering to said animal an effective amount of a compound of the Formula I, or a pharmaceutically-acceptable salt thereof, as claimed in claim 1.

10. A method for treating an inflammatory disease or medical condition in a warm blooded animal in need thereof, which comprises administering to said animal an effective amount of a compound of the Formula I, or a pharmaceutically-acceptable salt thereof, as claimed in claim 1.

11. The method of claim 10 wherein said inflammatory disease or medical condition is selected from rheumatoid arthritis, inflammatory bowel disease, glomerulonephritis and lung fibrosis.

12. A method of treating or preventing acute rejection of a transplanted organ or tissue is a warm blooded animal, which comprises administering to said animal an effective amount of a compound of the Formula I, or a pharmaceutically-acceptable salt thereof, as claimed in claim 1.

13. A method for producing an immunoregulatory or immunosuppressive effect in a warm blooded animal in need thereof for the prevention or treatment of tissue or organ rejection following transplant surgery, which comprises administering to said animal an effective amount of a compound of the Formula I, or a pharmaceutically-acceptable salt thereof, as claimed in claim 1.

14. A method of limiting T cell activation in a warm blooded animal in need thereof by inhibition of at least one tyrosine-specific protein kinase involved in early signal transduction, which comprises administering to said animal an effective amount of a compound of the Formula I, or a pharmaceutically-acceptable salt thereof, as claimed in claim 1.

15. The method of claim 14 wherein at least one said tyrosine-specific protein kinase is $P56^{lck}$.

* * * * *